(12) United States Patent
Matsui et al.

(10) Patent No.: US 6,458,081 B1
(45) Date of Patent: Oct. 1, 2002

(54) ULTRASONIC DIAGNOSTIC APPARATUS

(75) Inventors: Susumu Matsui; Akihiro Sano; Eiji Goto, all of Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/557,416

(22) Filed: Apr. 21, 2000

(30) Foreign Application Priority Data

| Apr. 23, 1999 | (JP) | 11-116385 |
| Aug. 11, 1999 | (JP) | 11-227697 |
| Nov. 12, 1999 | (JP) | 11-323257 |

(51) Int. Cl.[7] ................................................ A61B 8/00
(52) U.S. Cl. ..................................................... 600/437
(58) Field of Search ........................ 600/437, 440–441, 600/454–456

(56) References Cited

U.S. PATENT DOCUMENTS

| 5,553,620 | A | * | 9/1996 | Snider et al. | 600/440 |
| 5,911,133 | A | * | 6/1999 | Soble | 600/450 |
| 5,920,317 | A | * | 7/1999 | McDonald | 345/356 |
| 5,997,478 | A | * | 12/1999 | Jackson et al. | 600/437 |
| 6,001,061 | A | * | 12/1999 | Ogishima et al. | 600/440 |
| 6,063,030 | A | * | 5/2000 | Vara et al. | 600/437 |
| 6,149,594 | A | * | 11/2000 | Rock et al. | 600/437 |
| 6,287,257 | B1 | * | 9/2001 | Matichuk | 600/437 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

A workflow representing an operation procedure is displayed on a monitor as a status window to notify a user of the operation procedure. The workflow is defined by a workflow protocol in which activities of an ultrasonic diagnostic apparatus for realizing operations associated with diagnosis are arranged in accordance with the operation procedure. Since each function of the ultrasonic diagnostic apparatus is controlled in accordance with the workflow protocol, the ultrasonic diagnostic apparatus can perform a diagnostic operation according to the workflow using the functions according to the workflow protocol.

44 Claims, 27 Drawing Sheets

FIG. 4

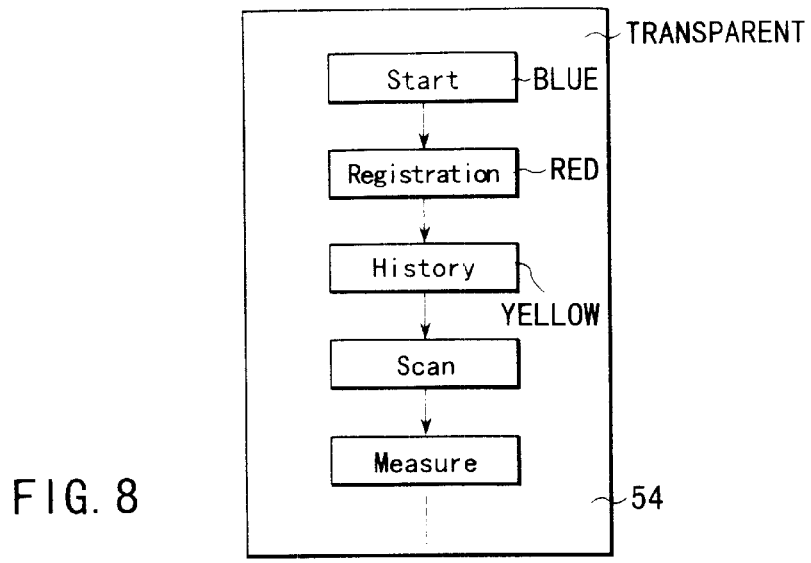

FIG. 8

| Execution State | Color | Shape | Display State |
|---|---|---|---|
| Unexecuted | Gray | Rectangle | Still |
| Execution In Progress | Blue | Rectangle | Still |
| Normal End | Dark Green | Rectangle | Still |
| Abnormal End | Red | Rectangle | × Mark |
| Interrupt | Dark Red | Rectangle | Black-Out |
| Restart | Green | Rectangle | Still |
| Warning | Yellow | Rectangle | Blinking |
| For Hierarchy | Any Of Above Colors | Rectangle With Double Frame | Still |
| Execution In Progress On Background | Dark Blue | Ellipsoid | Mark For Background |
| User Definition | Others | Freely Defined Icon | May Be Turned Off |

FIG. 9

| Activity | Display | | After Start |
|---|---|---|---|
| Start | On | → | On |
| Resitration | On | → | Off |
| History | On | → | On |
| Scan | On | → | Off |
| Measurement | On | → | Off |
| Print | On | → | On |
| Report | On | → | On |
| End | On | → | Off |

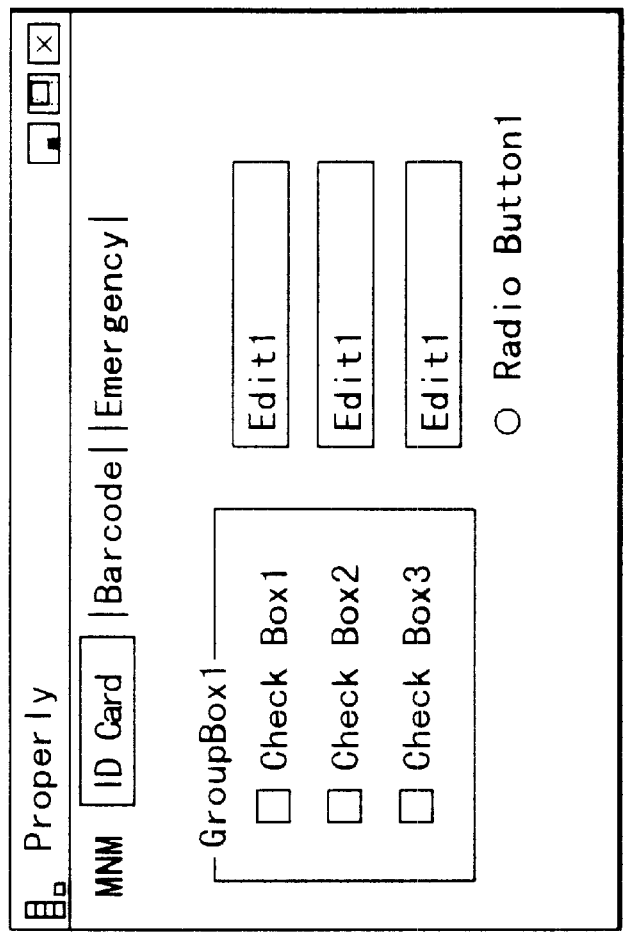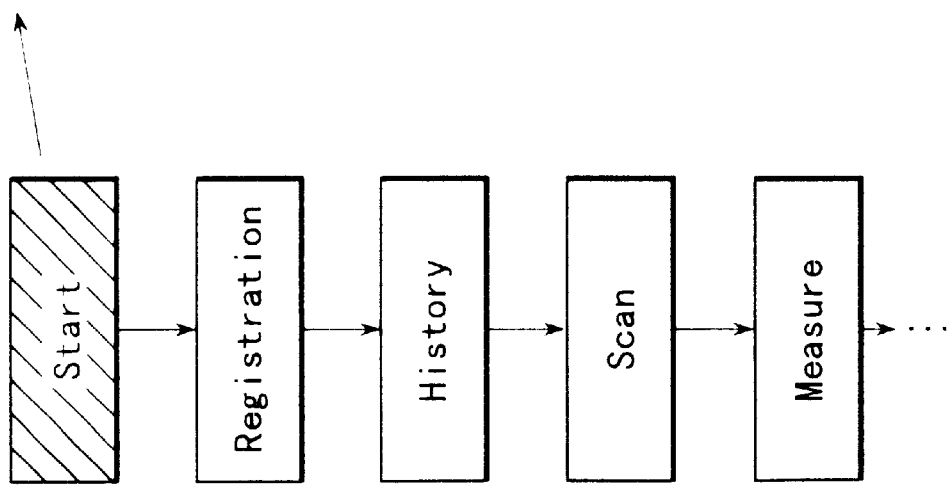
FIG. 12

(EXAMPLE 1)
C1=OUTPUT OF B < 10%
C2=10% < OUTPUT OF B < 50%
C3=OUTPUT OF B > 50%

(EXAMPLE 2)
C1=(A+B) < 10%
C2=10% < (A+B) < 50%
C3=(A+B) > 50%

| B out | Next |
|-------|------|
| 10%   | C1   |
| 20%   | C1   |
| 30%   | C2   |
| 40%   | C2   |
| 50%   | C2   |
| 60%   | C2   |
| 70%   | C2   |
| 80%   | C3   |
| 90%   | C3   |
| 100%  | C3   |

| User | Workflow Name | Workflow Protocol → | | | | | | | | | |
|---|---|---|---|---|---|---|---|---|---|---|---|
| Dr. A | Normal | Init | System Check | Preset | Patient Registration | Refer Previous Image | B Scan | Measure | Print | Report | Archive | |
| Dr. B | Stress Echo | Init | System Check | Preset | Patient Registration | B Scan | Stress Start | Injector Control | VCR | Measure | Report | Archive |
| Dr. C | Contrast Echo | Init | System Check | Preset | Patient Registration | B Scan | Contrast Injectio | Measure | Analyze | Print | Report | Archive |
| Dr. E | ACM | Init | System Check | Preset | Patient Registration | C Scan | ACM | Report | Archive | | | |
| Dr. F | TDI | Init | System Check | Preset | Patient Registration | TDI | Storage | MVG | Print | Report | Archive | |
| Dr. G | Normal | Init | System Check | Preset | Patient Registration | B Scan | Measure | Print | Report | Archive | | |
| Dr. H | Normal | Init | System Check | Preset | Patient Registration | Diagnosis A | Diagnosis B | Diagnosis C | Report | Archive | | |

FIG. 36

| Workflow STEPS |||||||
|---|---|---|---|---|---|---|
| Workflow | | HCC-Contrast#1 ||||||
| Patient Name | | Alex Zanardi || Patient ID | 990723002 ||
| Confidence ||| Measurement ||||
| ☑ | + | Mitral | Transmittal Flow ||||
| ☐ | ☐ | Tricuspid | E | 75 | 70-100cm/s |
| ☑ | ☐ | LVOT | A | 100 | 45-70cm/s |
| ☑ | + | Pulmonic | E/A | 0.75 | 1.0-1.5 |
| ☑ | + | Aorta | | | |
| ☑ | ☐ | Contrast2 | EF | 30 | 50-88% |
| ☐ | ☐ | | ES | 40 | 30-50% |

901 PROTOCOL CHECK    MEASUREMENT VALUE    NORMAL VALUE
                              903

DIAGNOSIS CHECK SHEET

930 — DIAGNOSTIC FINDING INPUT [ AMI ]

Name  Mr. XXXX          Date 99/10/17

| DIAGNOSTIC ITEM | DIAGNOSTIC RESULT | DISEASE DATA | COMMENT |
|---|---|---|---|
| MURAL MOTION ABNORMALITY | Yes | Yes | |
| DECREASE IN MURAL THICKNESS | Yes | Yes | |
| ECHO LUMINANCE | No Change | Increase | Re-Check |
| DECREASE IN DDR | Yes, 20mm/sec | Yes, 33mm/sec Or Less | |
| INCREASE IN A WAVE | Yes | Yes | |
| A/E RATIO | No. 1 | Yes, 1.02 Or More | Re-Measure |
| AC TIME | . . . | | |

ULTRASONIC DIAGNOSTIC APPARATUS

CROSS-REFERENCE TO RELATED APPLICATIONS

This application is based upon and claims the benefit of priority from the Japanese Patent Applications No. 11-116385, filed Apr. 23, 1999; No. 11-323257, filed Nov. 12, 1999; and No. 11-227697, filed Aug. 11, 1999, the entire contents of which are incorporated herein by reference.

BACKGROUND OF THE INVENTION

The present invention relates to an ultrasonic diagnostic apparatus which images the state of an internal organ or a blood flow using an ultrasonic wave and diagnoses it.

An ultrasonic image diagnostic apparatus is a diagnostic apparatus which irradiates a desired portion of an object (patient) with an ultrasonic wave and obtains a tomographic image of a soft tissue on the basis of the reflected wave from the object. In recent years, the performance of ultrasonic image diagnostic apparatuses is remarkably improved so that various examination methods and clinical applications to be described below are enabled.

Basic examination methods for ultrasonic diagnostic apparatuses include B-mode 2D tomography, a Doppler method called a PW or CW mode, a color Doppler method called a CDFM mode which images a blood flow, and in recent years, TDI (Tissue Doppler Imaging) which images the movement of a tissue, a 3D method of three-dimensionally displaying a tissue, and a 4D method of displaying a three-dimensional image as a moving image. These examination methods are executed in accordance with clinical applications such as a stress echo method, a contrast echo method, and ACM used to measure the cardiac output of a heart and therefore can provide useful clinical information about an object.

Such a variety of examination methods produce the following aspects in association with use of an ultrasonic diagnostic apparatus.

For example, to use an apparatus by exploiting the above-described various functions, many switching operations (keyboard, touch panel, trackball, mouse, and the like) are necessary. To exploit the various functions of individual examination methods, an operator such as a doctor or a technician must learn operation techniques for individual functions.

Generally, an examination by an ultrasonic diagnostic apparatus is comprised of a combination of a plurality of operations including acquisition of a plurality of data and image measurement. This combination changes in units of facilities (medical facilities such as hospitals and clinics, or diagnostic departments in one medical facility) where ultrasonic diagnostic apparatuses are installed. Even for examinations with the same contents, the operation procedure changes in units of operators (doctors or examination technicians). Hence, the variety of examination methods further increases the degree of freedom of examination operations.

Ultrasonic diagnostic apparatuses are becoming inexpensive. As the ultrasonic diagnostic apparatuses become inexpensive, they are being introduced not only in large hospitals but also in many other hospitals. Since the ultrasonic diagnostic apparatuses are widespread, the population of ultrasonic diagnostic apparatus users is steadily increasing, including skilled persons and beginners.

Under these circumstances, demand has arisen for an apparatus which can be easily operated by either a skilled person or a beginner in accordance with the degree of experience of the operator and realize accurate diagnosis.

BRIEF SUMMARY OF THE INVENTION

The present invention has been made in consideration of the above situation, and has as its object to provide an apparatus which can be easily operated by either a skilled person or a beginner in accordance with the degree of experience of the operator and realize accurate diagnosis.

The present invention according to the first aspect is an ultrasonic diagnostic apparatus which comprises: storage means for storing a plurality of operation procedures formed of activities each of which is defined by arrangement of activities constructed by at least one of functions of said ultrasonic diagnostic apparatus in a predetermined order; input means for inputting predetermined information in respect of diagnostic; selection means for selecting an operation procedure from the plurality of operation procedures on the basis of the information; display means for displaying the operation procedure selected by said selection means; and control means for executing each operation corresponding to each activity in accordance with the displayed operation procedure.

The present invention according to the second aspect is an ultrasonic diagnostic apparatus which comprises: storage means for storing a plurality of operation procedures formed of activities each of which is defined by arrangement of activities constructed by at least one of functions of said ultrasonic diagnostic apparatus in a predetermined order; input means for inputting predetermined information in respect of diagnostic; selection means for selecting a operation procedure from the plurality of operation procedures on the basis of the information; display means for displaying the operation procedure selected by said selection means; activity selection means for selecting an activity which composes the displayed operation procedure, in accordance with an instruction by operator; and control means for executing an operation corresponding to the activity according to the displayed operation procedure in order and, if an activity is selected by said activity selection means, executing an operation corresponding to the activity selected by said activity selection means.

The present invention according to the third aspect is an ultrasonic diagnostic apparatus which comprises: storage means for storing a plurality of operation procedures formed of activities each of which is defined by arrangement of activities constructed by at least one of functions of said ultrasonic diagnostic apparatus in a predetermined order; input means for inputting predetermined information in respect of diagnostic; selection means for selecting an operation procedure from the plurality of operation procedures on the basis of the information; display means for displaying the operation procedure selected by said selection means; change means for changing composition of the displayed operation procedure in such a manner that a predetermined activity is added to the displayed operation procedure or is omitted from the displayed operation procedure at an arbitrary timing; and control means for executing an operation corresponding to the activity which composes a changed operation procedure in a case that the displayed operation procedure is changed by said change means and executing an operation corresponding to the activity which composes the selected operation procedure in a case that the displayed operation procedure is not changed.

The present invention according to the fourth aspect is an ultrasonic diagnostic apparatus which comprises: storage means for storing a plurality of operation procedures each of which arranges activities constructed by at least one of functions of said ultrasonic diagnostic apparatus in a predetermined order to define an operation procedure; input means for inputting predetermined information in respect of diagnostic; selection means for selecting a operation procedure from the plurality of operation procedures on the basis of the information; display means for displaying the operation procedure selected by said selection means and, if an activity selected by operator is associated with a sub-operation procedure, displaying the sub-operation procedure; and control means for executing control of an activity selected from the activities which compose the displayed operation procedure or the displayed sub-operation procedure.

The present invention according to the fifth aspect is an ultrasonic diagnostic apparatus which comprises: storage means for storing a plurality of operation procedures formed of activities each of which contains branched operations and is defined by arrangement of activities constructed by at least one of functions of said ultrasonic diagnostic apparatus in a predetermined order; input means for inputting predetermined information in respect of diagnostic; selection means for selecting a operation procedure from the plurality of operation procedures on the basis of the information; display means for displaying the operation procedure selected by said selection means in such a manner that the selected operation procedure contains branches of an operation; and control means for executing operation corresponding to each activity in order according to the displayed operation procedure.

The present invention according to the sixth aspect is an ultrasonic diagnostic apparatus which comprises: storage means for storing a plurality of examination item lists corresponding to a plurality of data acquisition items and measurement items; selection means for selecting an examination item list from the plurality of the examination item lists; data acquisition and measurement means for executing an data acquisition and a measurement corresponding to a data acquisition item and a measurement item on the selected examination item list; and display means for displaying simultaneously the data acquisition item and the measurement item corresponding to the selected examination item list and a mark which represents whether the data acquisition or the measurement is executed; and change means for changing whether the displayed acquisition or the displayed measurement is executed, by manual operation.

The present invention according to the seventh aspect is an ultrasonic diagnostic apparatus which comprises: storage means for storing a plurality of examination lists corresponding to a plurality of data acquisition items and measurement items; selection means for selecting an examination item list from the plurality of examination item lists; data acquisition and measurement means for executing data acquisition and a measurement corresponding to the data acquisition item and the measurement item on the selected examination item list; and display means for displaying simultaneously the data acquisition item and the measurement item corresponding to the selected examination item list and a mark which represents whether each of the data acquisitions and the measurements is executed; and communication means for transmitting/receiving information of the examination item list through a network.

The present invention according to the eighth aspect is an ultrasonic diagnostic apparatus which comprises: storage means for storing a plurality of operation procedures formed of activities each of which is defined by arrangement of a plurality of data acquisition items and measurement items in a predetermined order; control means for executing data acquisitions and measurements corresponding to the plurality of the data acquisition items and the measurement items on the plurality of the examination item lists; and output means for outputting data in respect of the plurality of the data acquisition items and the measurement items in a predetermined format.

The present invention according to the ninth aspect is a control method of a ultrasonic diagnostic apparatus which comprises the steps of: selecting a predetermined operation procedure from a plurality of operation procedures formed of activities, stored in advance, each of which is defined by arrangement by activities constructed by at least one of functions of said ultrasonic diagnostic apparatus in a predetermined order on the basis of information in respect of diagnostic; displaying the selected operation procedure; and executing each operation corresponding to each activity in accordance with the displayed operation procedure.

The present invention according to the tenth aspect is a control method of a ultrasonic diagnostic apparatus which comprises the steps of: selecting a predetermined operation procedure from a plurality of operation procedures formed of activities, stored in advance, each of which arranges activities constructed by at least one of functions of said ultrasonic diagnostic apparatus in a predetermined order on the basis of information in respect of diagnostic; displaying the selected operation procedure; selecting an activity which composes the displayed operation procedure, in accordance with an instruction by operator; executing each operation corresponding to each activity in accordance with the displayed operation procedure in order; and executing an operation corresponding to a selected activity if an another activity is selected in progress of the each operation.

The present invention according to the eleventh aspect is a control method of an ultrasonic diagnostic apparatus which comprises the steps of: selecting a predetermined operation procedure from a plurality of operation procedures formed of activities, stored in advance, each of which is defined by arrangement of activities constructed by at least one of functions of said ultrasonic diagnostic apparatus in a predetermined order on the basis of information in respect of diagnostic; displaying the selected operation procedure; selecting an activity which composes the displayed operation procedure, in accordance with an instruction by operator; changing composition of the displayed operation procedure in such a manner that a predetermined activity is added to the displayed operation procedure or is omitted from the displayed operation procedure at an arbitrary timing; and executing an operation corresponding to the activity which composes a changed operation procedure.

The present invention according to the twelfth aspect is a control method of a ultrasonic diagnostic apparatus which comprises the steps of: selecting a predetermined operation procedure from a plurality of operation procedures formed of activities, stored in advance, each of which arranges activities constructed by at least one of functions of said ultrasonic diagnostic apparatus in a predetermined order on the basis of information in respect of diagnostic; displaying the selected operation procedure; displaying a sub-operation procedure if an activity selected by operator, which composes the displayed operation procedure, is associated with a sub-operation procedure; and executing control of the activity selected from the activities which compose the displayed operation procedure or the displayed sub-operation procedure.

The present invention according to the thirteenth aspect is a control method of a ultrasonic diagnostic apparatus which comprises the steps of: selecting a predetermined operation procedure from a plurality of operation procedures formed of activities, stored by storage means, each of which contains branched operations and is defined by arrangement of activities constructed by at least one of functions of said ultrasonic diagnostic apparatus in a predetermined order on the basis of inputted information in respect of diagnostic; displaying the selected operation procedure in such a manner that the selected operation procedure contains branches of an operation; and executing operation corresponding to the each of activities in order according to the displayed operation procedure.

The present invention according to the fourteenth aspect is a control method of a ultrasonic diagnostic apparatus which comprises the steps of: selecting a predetermined examination item list from a plurality of examination item lists, stored in advance, each of which corresponds to a plurality of data acquisition items and measurement items; executing each data acquisition and a measurement in respect to each of the data acquisition item and the measurement item composes the selected examination item list; displaying simultaneously the data acquisition item and the measurement item corresponding to the selected examination item list and a mark which represents whether the data acquisition or the measurement is executed; and changing the mark which represents whether the displayed acquisition or the displayed measurement is executed by manual operation.

The present invention according to the fifteenth aspect is a control method of a ultrasonic diagnostic apparatus which comprises the steps of: selecting an examination item list from a plurality of examination lists which is stored in advance and is composed of a plurality of data acquisition items and measurement items; executing an data acquisition and a measurement corresponding to the data acquisition item and the measurement item on the selected examination item list; and displaying simultaneously the data acquisition item and the measurement item corresponding to the selected examination item list and a mark which represents whether each of the data acquisitions and the measurements is executed; and transmitting/receiving a information of the examination item list through a network.

The present invention according to the sixteenth aspect is a control method of a ultrasonic diagnostic apparatus which comprises the steps of: executing data acquisitions and measurements corresponding to a plurality of operation procedures each of which is stored in advance and defined by arrangement of a plurality of data acquisition items and measurement items in a predetermined order; and outputting data in respect of the plurality of the data acquisition items and the measurement items in a predetermined format.

According to any one of the aspects described above, an ultrasonic diagnostic apparatus can be easily operated by either a skilled person or a beginner in accordance with the degree of experience of the operator and realize accurate diagnosis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a view showing a status window 30 of a workflow 31, and a registration sheet 34, which are displayed on a monitor 20.

FIG. 8 is a view for explaining the display form of the status window 30.

FIG. 9 is a view showing examples of symbol display forms according to operative states of an activity.

FIG. 12 is a view showing a window for setting the attribute of the "Start" activity.

FIG. 36 is a view showing an example of a protocol setting sheet 80 used to manually set a workflow protocol.

FIG. 43 is a view showing a diagnosis check sheet.

DETAILED DESCRIPTION OF THE INVENTION

The first to fifth embodiments of the present invention will be described below with reference to the accompanying drawing.

First Embodiment

Figure 1:
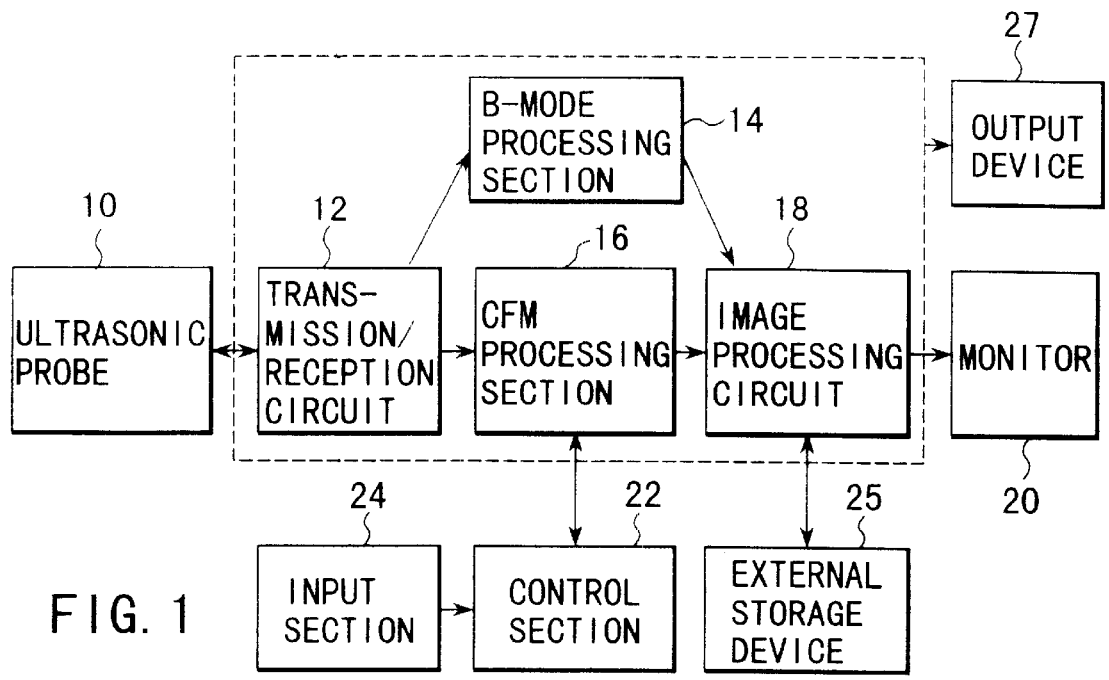
FIG. 1 is a block diagram showing the schematic arrangement of an ultrasonic diagnostic apparatus according to the present invention.

FIG. 1 shows the schematic arrangement of an ultrasonic diagnostic apparatus according to the present invention.

The arrangement of the ultrasonic diagnostic apparatus according to the present invention will be described first with reference to FIG. 1.

An ultrasonic probe 10 is a contact for transmitting/receiving an ultrasonic wave to/from a patient and is formed from a piezoelectric element.

A transmission/reception circuit 12 sends a driving signal to the ultrasonic probe 10 in accordance with a selected mode. The transmission/reception circuit 12 also performs delay/addition processing for an ultrasonic echo signal sent from the ultrasonic probe 10 and transmits the signal to a B-mode processing section 14 and CFM (Color Flow Mapping) processing section 16 on the output side.

The B-mode processing section 14 detects an envelope from the reception signal received from the transmission/reception circuit 12 and sends the detected signal to an image processing circuit 18. The signal output from the B-mode processing section 14 represents form information of a tissue.

The CFM processing section 16 obtains velocity information from the electrical signal received from the transmission/reception circuit 12 by frequency analysis and sends the analysis result to the image processing circuit 18. The signal output from the CFM processing section 16 represents moving velocity information of a blood flow or tissue.

The image processing circuit 18 receives the signals from the B-mode processing section 14 and CFM processing section 16, converts them into a TV scan signal, and sends the signal to a monitor 20.

The monitor 20 serves as a display means for displaying a sensed ultrasonic image and workflow (to be described later) as a status window.

A control section 22 has a function of an information processing unit (computer) and serves as a control means for controlling the operation of an ultrasonic diagnostic apparatus 1. The control section 22 executes a workflow system (to be described later).

An input section 24 comprises a keyboard or mouse which serves as an interface used by an operator to input various instructions to the ultrasonic diagnostic apparatus.

An external storage device 25 is constructed by, e.g., an HDD (Hard Disk Drive), DVD (Digital Video Disk), or CD (Compact Disk). This storage device stores ultrasonic image data sensed by the ultrasonic diagnostic apparatus, or image data, measurement data, or finding data of each patient, which is obtained by another diagnostic apparatus (for example, an MRI diagnostic apparatus, CT diagnostic apparatus, or X-ray diagnostic apparatus). Each stored data has an identifier such as a patient ID and is managed on the basis of the identifier.

An output device 27 outputs a print of a sensed ultrasonic image or various kinds of information according to ultrasonic diagnosis.

(Workflow System)

A workflow system executed by the control section 22 will be described next.

A workflow system is realized by executing, in the control section 22, dedicated workflow system software (workflow system program) supplied by a recording medium such as a CD-ROM, floppy disk, hard disk, or memory card, or a communication medium such as a network.

A workflow is an operation procedure (flow) necessary for predetermined diagnosis. One function of the ultrasonic diagnostic apparatus is defined as a basic activity, and a composite function defined by a plurality of basic activities is defined as a composite activity. An activity which is constructed by a plurality of basic or composite activities for realizing a specific operation and executes a selected one of the plurality of activities is defined as a candidate activity. As described above, a workflow is a flow chart showing an operation procedure required for predetermined diagnosis. A protocol which defines a workflow by activities for realizing each operation of the workflow is called a workflow protocol. In the workflow protocol, activities necessary for predetermined diagnosis are arranged in a predetermined order. A control system for an ultrasonic diagnostic apparatus using a workflow is called a "workflow system".

These terms will be listed below.

Workflow: operation procedure (flow) necessary for predetermined diagnosis

Basic activity: one function of the ultrasonic diagnostic apparatus

Figure 2:
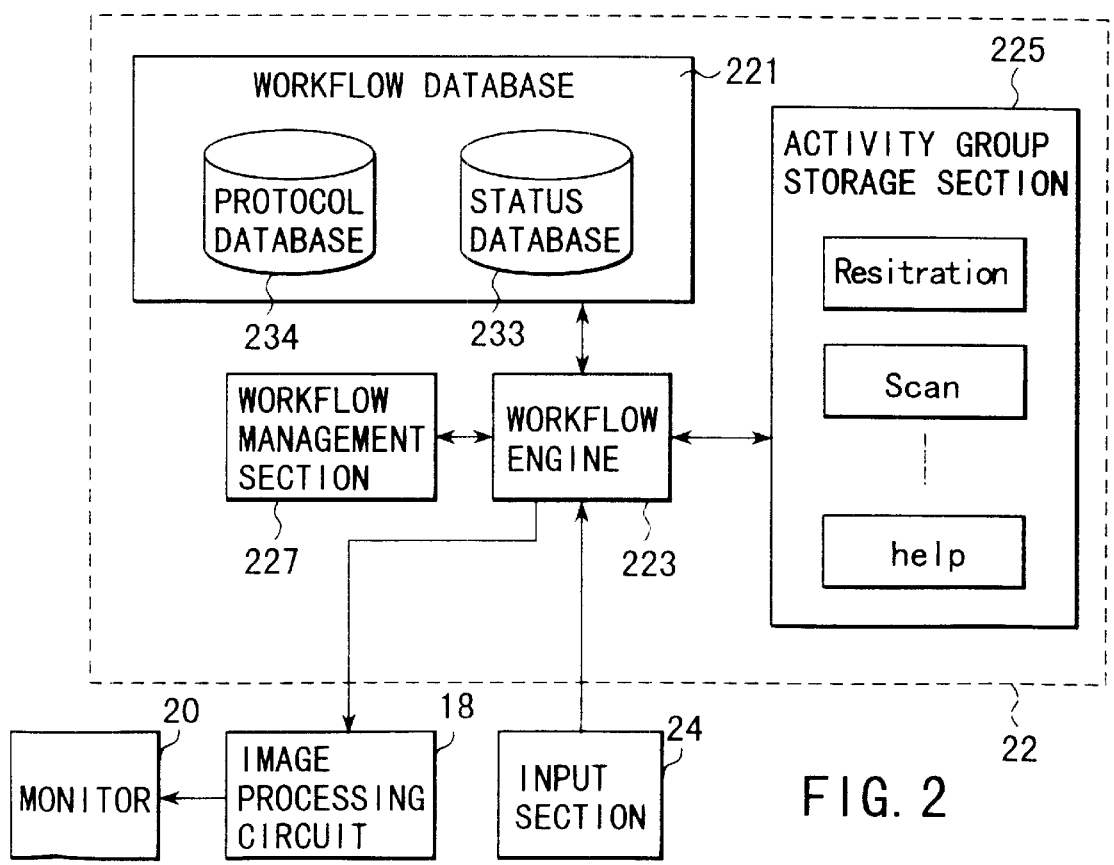
FIG. 2 is a block diagram showing the schematic arrangement of a workflow system.

Composite activity: composite function defined by a plurality of basic activities Candidate activity: function which is constructed by a plurality of basic or composite activities and realizes a specific operation by executing an arbitrarily selected activity Workflow protocol: protocol constructed by arranging activities necessary for predetermined diagnosis in a predetermined order and defining functions of an ultrasonic diagnostic apparatus in correspondence with operations of ultrasonic diagnosis Workflow system: control system for an ultrasonic diagnostic apparatus using a workflow FIG. 2 is a block diagram showing the schematic arrangement of a workflow system to be executed by the control section 22.

Referring to FIG. 2, a workflow engine 223 serves as a driving means for making the ultrasonic diagnostic apparatus 1 execute each activity of a workflow. The execution order of activities is normally the same as the arrangement order of a workflow protocol, though it can be arbitrarily changed by operator's manual operation. This will be described later. The workflow engine 223 also stores status information of a workflow in progress in a workflow database 221 or returns a status in response to an external inquiry.

The workflow database 221 has a template database 231, status information database 233, and protocol database 234.

The template database 231 stores workflow templates necessary for driving the workflow system. A workflow template means a data format associated with activity execution control. The workflow template will be described later in detail with reference to FIGS. 17 to 34.

The status information database 233 stores status and activity information associated with a workflow. Status information associated with a workflow means information for notifying the user of the contents or progress state of a workflow or sub flow (to be described later), or information representing the names of a workflow and activities constructing the workflow, current progress state (normal, continue, or end), start and end times, and time required to execute each activity.

The protocol database 234 stores workflow protocols. Each protocol stored in this database is defined in advance. The operator can newly define a protocol corresponding to a desired workflow by an editing function (to be described later) and add the protocol to the database 234.

An activity group storage section 225 is a storage means for storing starting programs of various activities. The activity programs are read out and started in accordance with the arrangement order of the workflow protocol (i.e., the order of a workflow).

A workflow management section 227 is a control means for displaying a workflow status in a window on the monitor or controlling to interrupt or stop a workflow in progress in accordance with an external input.

A case wherein diagnosis is done using the above workflow system will be described next.

Figure 3:
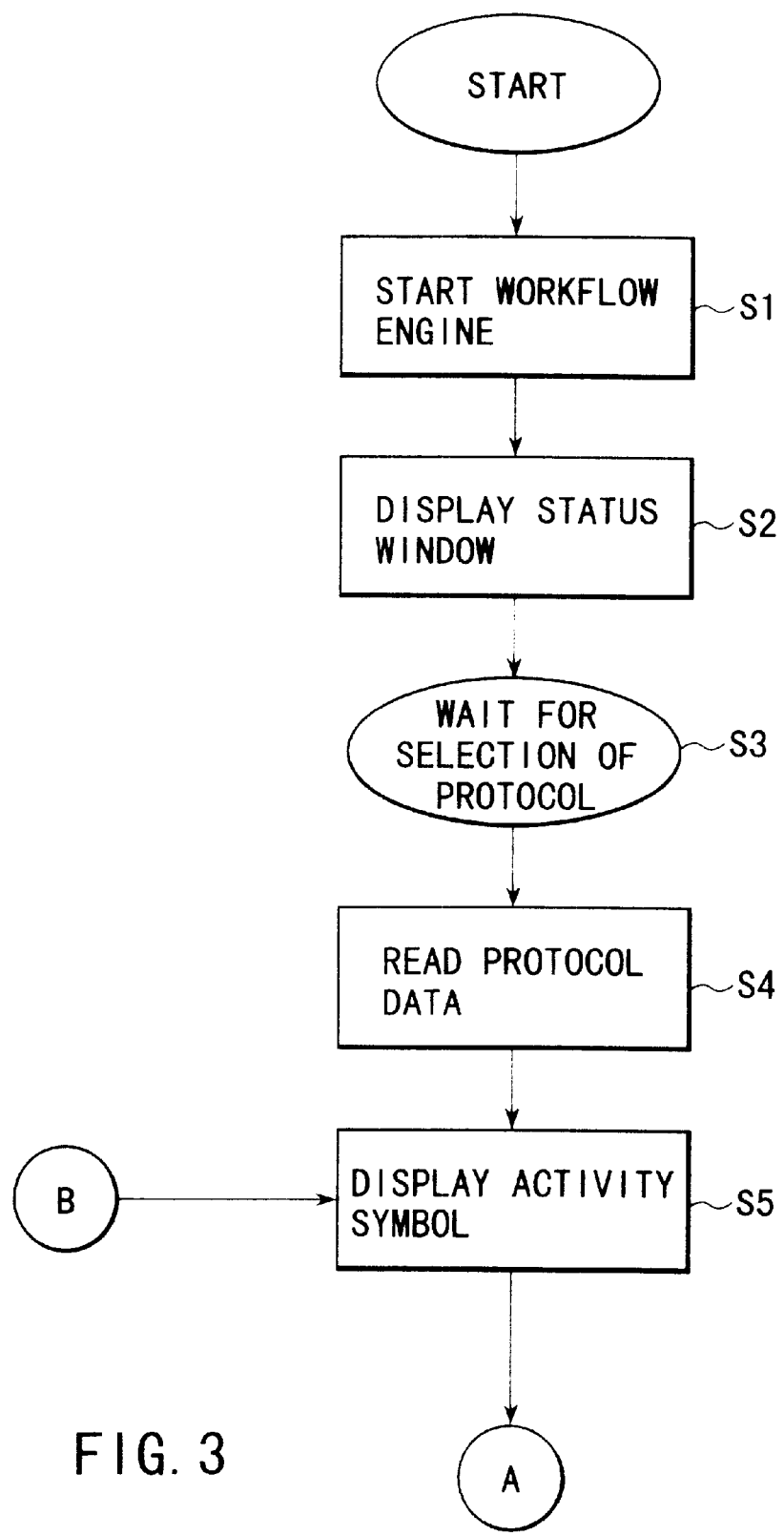
FIG. 3 is a flow chart showing the operation of a control section 22.

FIG. 3 is a flow chart showing the operation of the control section 22, in which the workflow system is activated, data associated with a patient, disease of the patient, and user (doctor or medical technician) are registered, and an appropriate workflow is selected on the basis of the contents of data.

Referring to FIG. 3, first, the workflow engine 223 is started by a predetermined operation from the input section 24 to activate the workflow system (step S1).

Figures 10, 11:
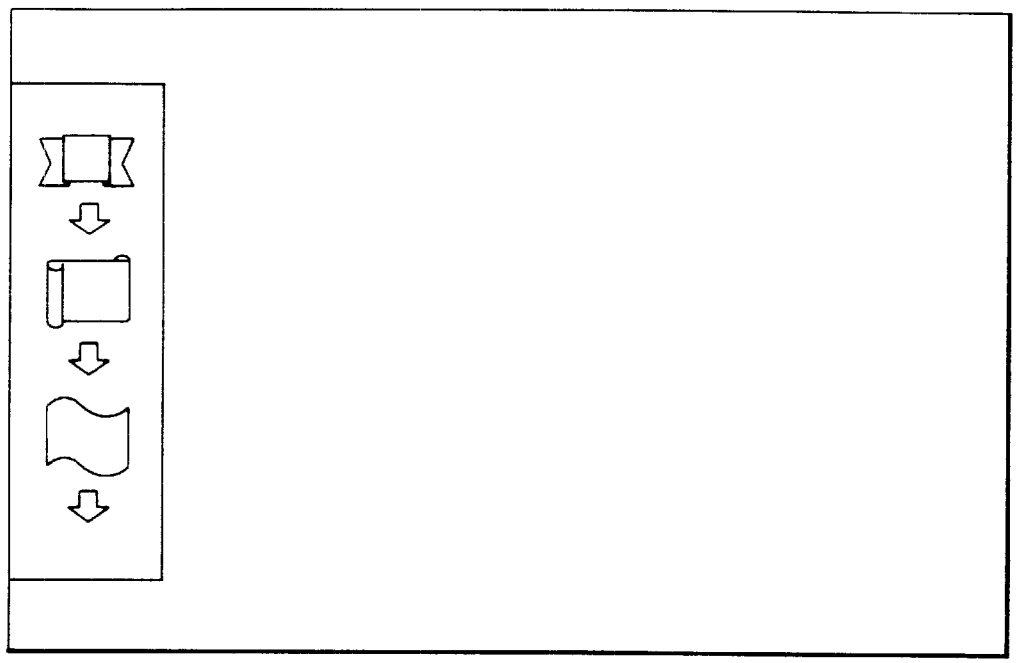
FIG. 10 is a view showing an example in which the shapes of symbols displayed in the status window 30 are discriminated in units of activities.
FIG. 11 is a view showing a situation in which the display ON/OFF timing is set in accordance with the contents of each activity.

When the workflow engine 223 starts, the workflow management section 227 displays a status window associated with a workflow on the monitor 20 (step S2). A status window means a window in which the status information of a workflow is displayed. The status information of a workflow and activities are provided in a display form of such status window (FIGS. 9 and 10).

Figure 4:
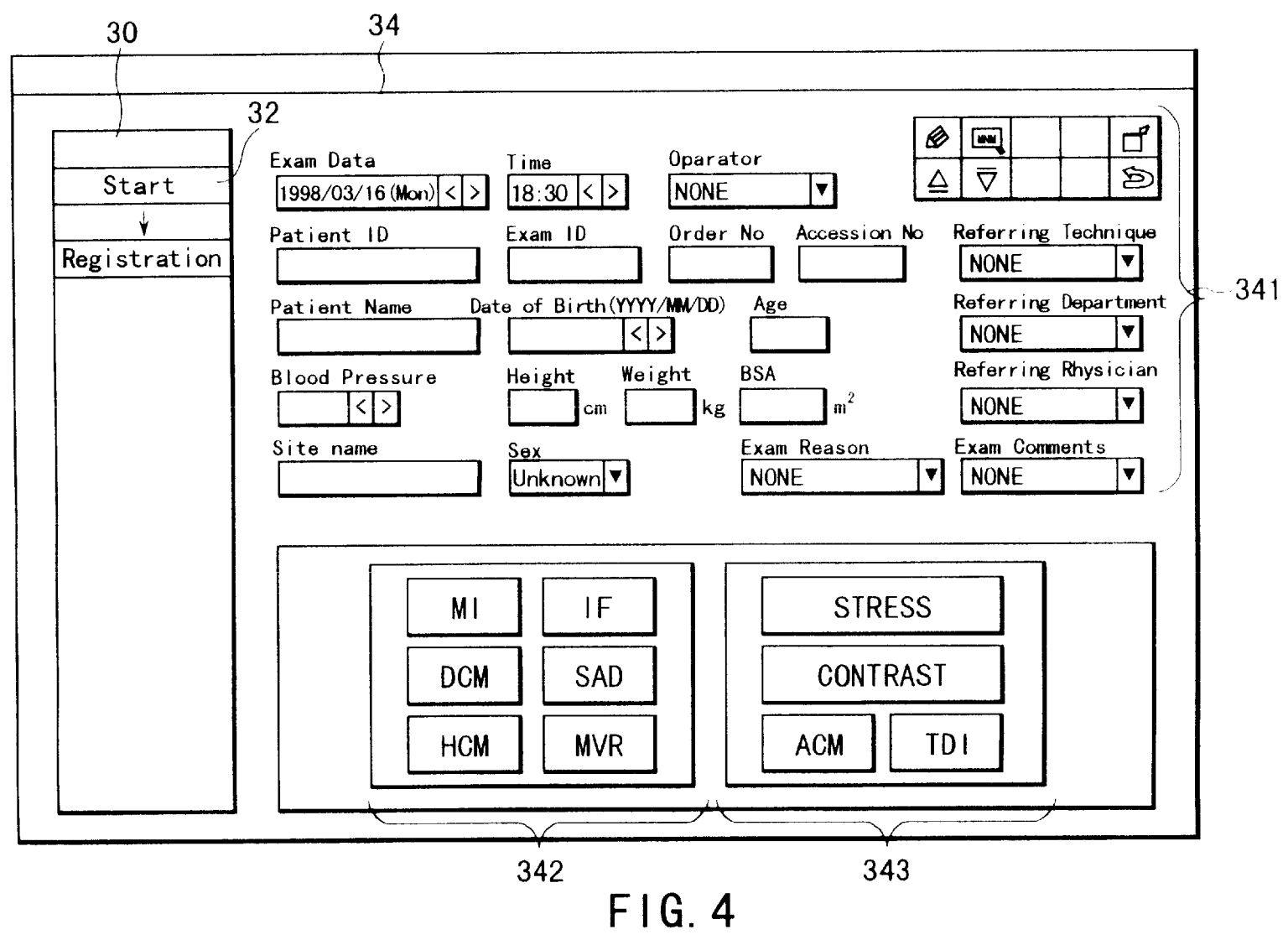

Referring to FIG. 4, a reference numeral 30 denotes a status window displayed on the monitor 20 immediately after activation of the workflow system. In the status window 30, only two activities "Start" and "Registration" are displayed. This is because no information of an operator or patient is input, and no diagnosis contents are determined currently. A workflow next to the two items is determined by the activity called "Registration" in the following way.

When the "Registration" window in the status window 30 is selected by the user, the workflow engine 223 starts the "Registration" activity stored in the activity group storage section 225. This "Registration" activity is a function of registering various items necessary for diagnosis in accordance with a registration sheet 34 shown in FIG. 4 and reading out an appropriate workflow from the template database 231 on the basis of the registered contents.

The registration sheet 34 has, for example, the following items.

The registration sheet 34 comprises a patient data item 341 for registering various data, including a patient ID, associated with a patient, a disease name item 342 for registering the name of disease of the patient, and a clinical application registration item 343 for registering a clinical application. The user registers items necessary for each diagnosis in accordance with the window shown in FIG. 4. From the viewpoint of safety, data associated with the user (operator) are preferably input when the ultrasonic diagnostic apparatus is activated. Alternatively, items related to the user may be added to the registration sheet 34.

The workflow management section 227 writes the input registration data in the template database 231. The workflow engine 223 selects a workflow protocol to be applied to the diagnosis from the template database 231 on the basis of, e.g., the registered disease name (step S3). The workflow engine 223 reads out a corresponding workflow protocol from the protocol database 234 and starts the protocol (step S4).

In the above description, a workflow protocol is selected on the basis of the registered disease name. However, various criteria can be used for this selection. For example, when a special diagnostic operation need be added for a certain patient, a workflow protocol for this patient may be stored in advance, and the corresponding workflow protocol may be selected on the basis of the patient ID input to the registration sheet 34. If individual users (doctors or medical technicians) have different operation procedures preferable for them, workflow protocols may be stored in units of users in advance, and a corresponding workflow protocol may be selected on the basis of an input disease name and user ID. Alternatively, one of workflow protocols which are defined and stored in units of diagnostic departments or medical associations in advance may be selected. Also, instead of using an existing workflow, a new workflow protocol can be manually set. This manual setting of a workflow protocol will be described in the second embodiment.

The workflow management section 227 displays the symbols of activities constructing the readout workflow protocol in the status window 30 displayed in step S2 in accordance with the progress order (step S5).

Figure 5:
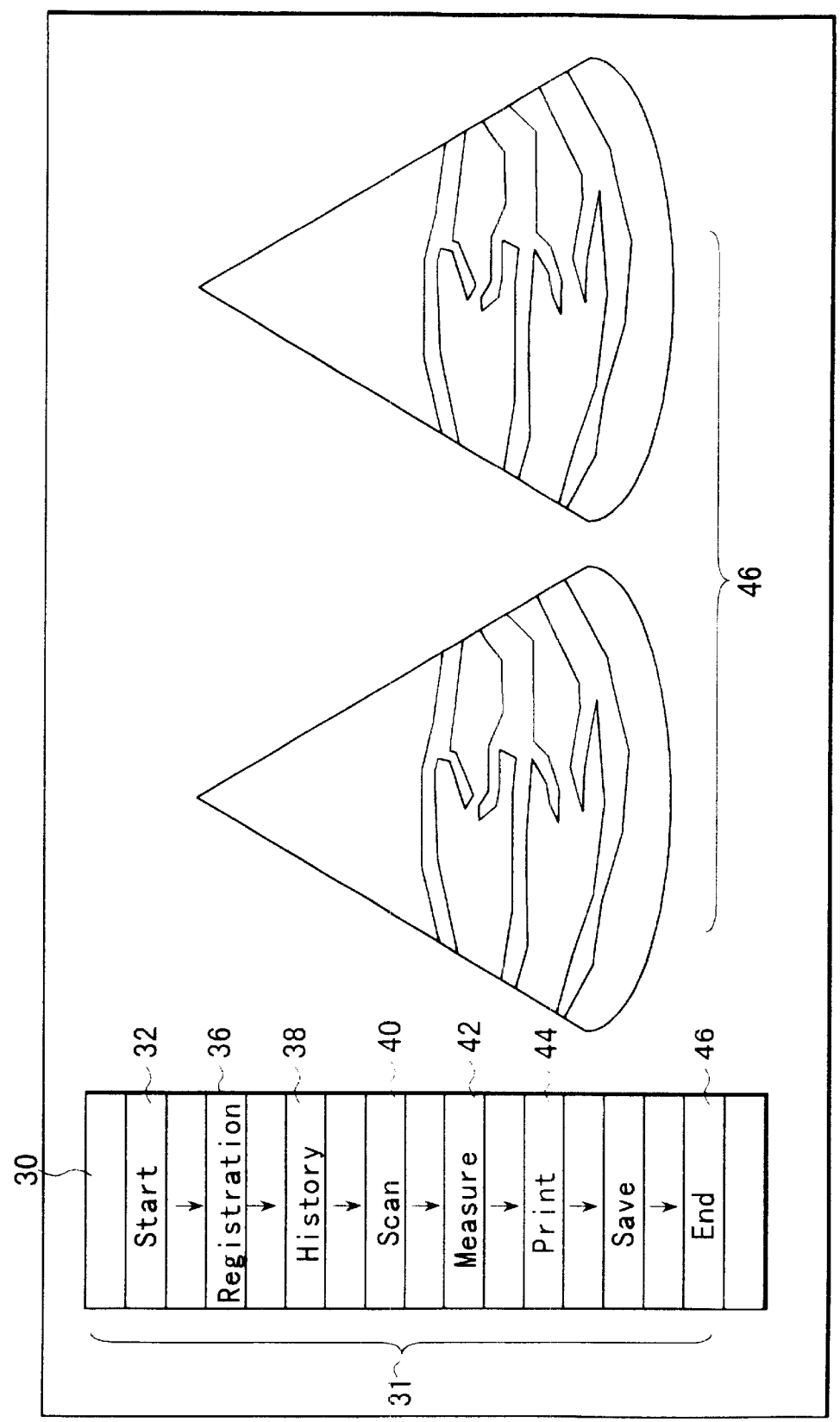
FIG. 5 is a view showing the status window 30 of the workflow 31, which is displayed on the monitor 20 after determination of a workflow protocol.

FIG. 5 shows the status window 30 of a workflow defined by the selected workflow protocol. In this workflow displayed as the status window 30, the symbols of activities of a diagnostic operation are sequentially arranged and displayed. Hence, the user can progress diagnosis in accordance with this workflow.

In the status window 30, the symbols of activities "History", "Scan", "Measure", "Print", "Save", and "End" are displayed in addition to "Start" and "Registration".

The functions of these activities are listed below.

"Start": function of (re)starting the workflow system

"Registration": function of registering various items necessary for diagnosis in accordance with the registration sheet 34 and determining and reading out an appropriate workflow on the basis of the registered contents "History": function of displaying a past ultrasonic image for reference "Scan": function of scanning an ultrasonic wave in the object to obtain an ultrasonic image "Measure": function of executing various measurement operations on the basis of the ultrasonic image "Print": function of printing various data "Save": function of saving various data "End": function of terminating the workflow system Each activity can be started by double-clicking a cursor on the symbol. For example, when an activity corresponding the symbol "History" is selected and started, past ultrasonic images 46 are displayed in parallel on the monitor 20, as shown in FIG. 5.

Next, the display form of the status window 30 will be described in the order of display timing, display position, window type, and display colors.

The display timing of the status window 30 will be described first.

Figure 6A:
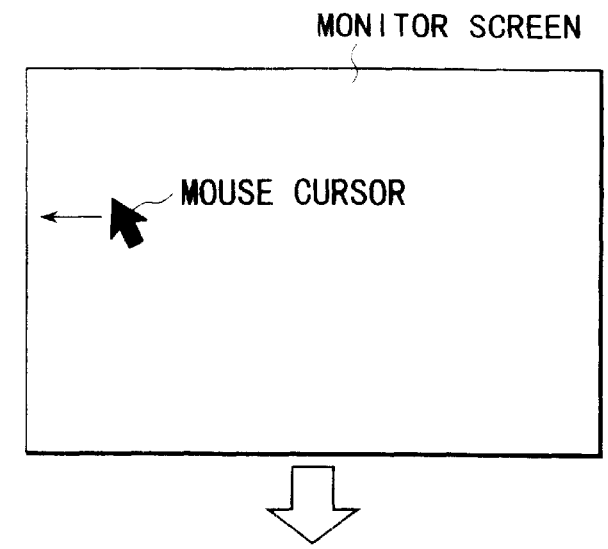
FIGS. 6A and 6B are views for explaining the display form of the status window 30.
Figure 6B:
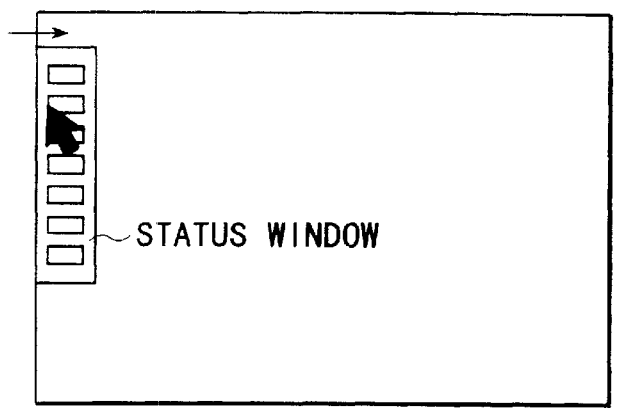

The status window notifies the user of the status information of a workflow (operation procedure). Hence, the status window need not always be kept displayed and is preferably turned on/off, as needed. For example, the status window 30 may be normally kept OFF, as shown in FIG. 6A, and redisplayed by moving the cursor point to a predetermined position (left edge of the window in FIG. 6A), as shown in FIG. 6B. An input key for displaying the status window 30 may be prepared on the operation panel or touch command screen such that the status window is displayed only when an instruction is input by the key. Alternatively, the status window may be automatically turned on/off by defining, in units of activities of the workflow protocol, whether the status window need be displayed (FIG. 11; this arrangement will be described later).

According to this arrangement, the status window 30 can be displayed at a timing desired by the user. In addition, the status window 30 can be displayed without impeding display of an ultrasonic image or the like. Hence, the screen of the monitor 20 can be more efficiently used.

The display position of the status window 30, window type, and display colors will be described next.

Figure 7:
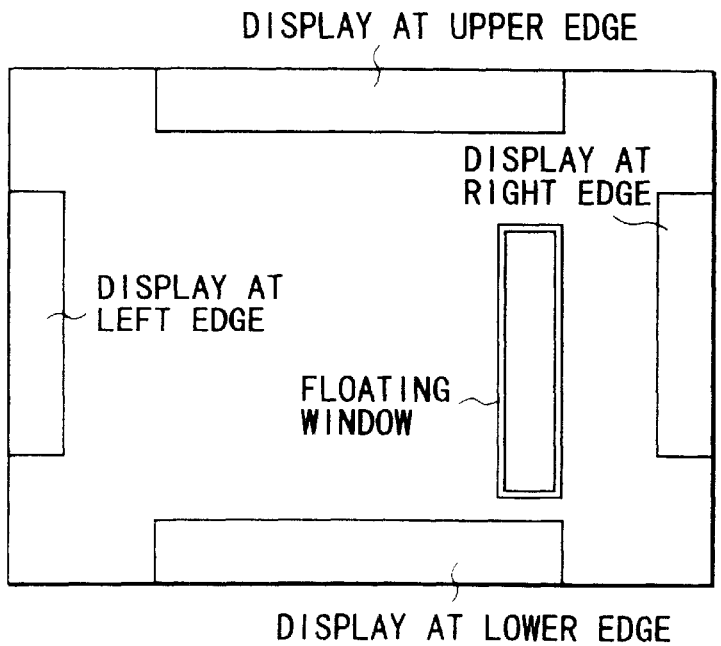
FIG. 7 is a view for explaining the display form of the status window 30.

The status window 30 can be displayed at any position on the screen, as shown in FIG. 7. The displayed window can be of either a fixed window type or a floating window type. Any colors can be used for the window. For example, as shown in FIG. 8, the display region except the status window 30 can be widened by displaying only the activity symbols in colors on a transparent background 54.

According to this arrangement, since a desired position, window type, and colors can be set for display of the workflow, a window convenient to see can be set in units of users.

Next, the symbol display form of each activity in the status window 30 will be described.

The status window 30 shows the progress state of a workflow or operative state of each activity. Hence, each activity symbol is preferably displayed to allow determination of the operative state of the activity, including "unexecuted", "execution in progress", "normal end", "abnormal end", "interrupt", "re-execute", and "warning". As will be described later, a corresponding activity may have a hierarchical structure. At this time, a plurality of functions may be simultaneously executed, or some functions may be executed as a background flow. In such a case, the operative state can preferably be determined.

In the ultrasonic diagnostic apparatus according to the present invention, the display forms of activity symbols are discriminated in accordance with the operative states. For example, the display color, shape, and display method (still display, blinking display, black-out display, or display-off) of each activity symbol are discriminated on the basis of the operation situation. This arrangement makes it easy to determine the operative state of each activity.

FIG. 9 is a view showing examples of symbol display forms according to operative states of an activity.

These forms are selected from a plurality of programs of colors, shapes, and display forms registered in advance. Alternatively, the forms may be manually set by the user. The set contents are preferably previewed. The set contents may be registered by the user (technician or doctor), and for example, setting for display may be automatically switched by inputting the user name.

FIG. 10 is a view showing an example in which the shapes of symbols displayed in the status window 30 are discriminated in units of activities.

All activities constructing a workflow protocol need not always be displayed in the workflow. For example, as shown in FIG. 11, the ON/OFF timing of each activity may be set in advance in accordance with the contents of the activity.

Hence, the user can easily determine the status of each activity. This is because the arrangement makes it possible to display each symbol in a unique color, shape, and form in accordance with the operative state of a corresponding activity. Since status display of an unwanted activity can be turned off, the user can do desired window setting.

Normally, setting of preset parameters of each activity (for example, focal depth of the "Scan" activity) is systematically managed. To change setting of preset parameters, a preset window is started, and a corresponding item is searched for and set. However, from the viewpoint of efficient operation, parameters associated with an activity are preferably set directly from the symbol displayed in the status window 30. To realize this parameter setting from a displayed symbol, for example, the operator moves the cursor onto a symbol using a mouse or a trackball and clicks the right button of the mouse to directly display a window for setting parameters associated with an activity corresponding to the displayed symbol. A dedicated set button may be prepared on the panel. FIG. 12 shows a window for setting the attribute of the "Start" activity by the above-described operation. As will be described later, parameter setting from a displayed symbol is a kind of interrupt processing executed in accordance with a workflow shown in FIG. 30 (to be described later).

This arrangement can further improve the operability because parameters associated with an activity can be directly set at an arbitrary timing.

The operation of the workflow system according to the workflow 31 from the activity "Scan" shown in FIG. 5 will be described below with reference to the workflow 31 and the flow chart shown in FIG. 13.

Figure 13:
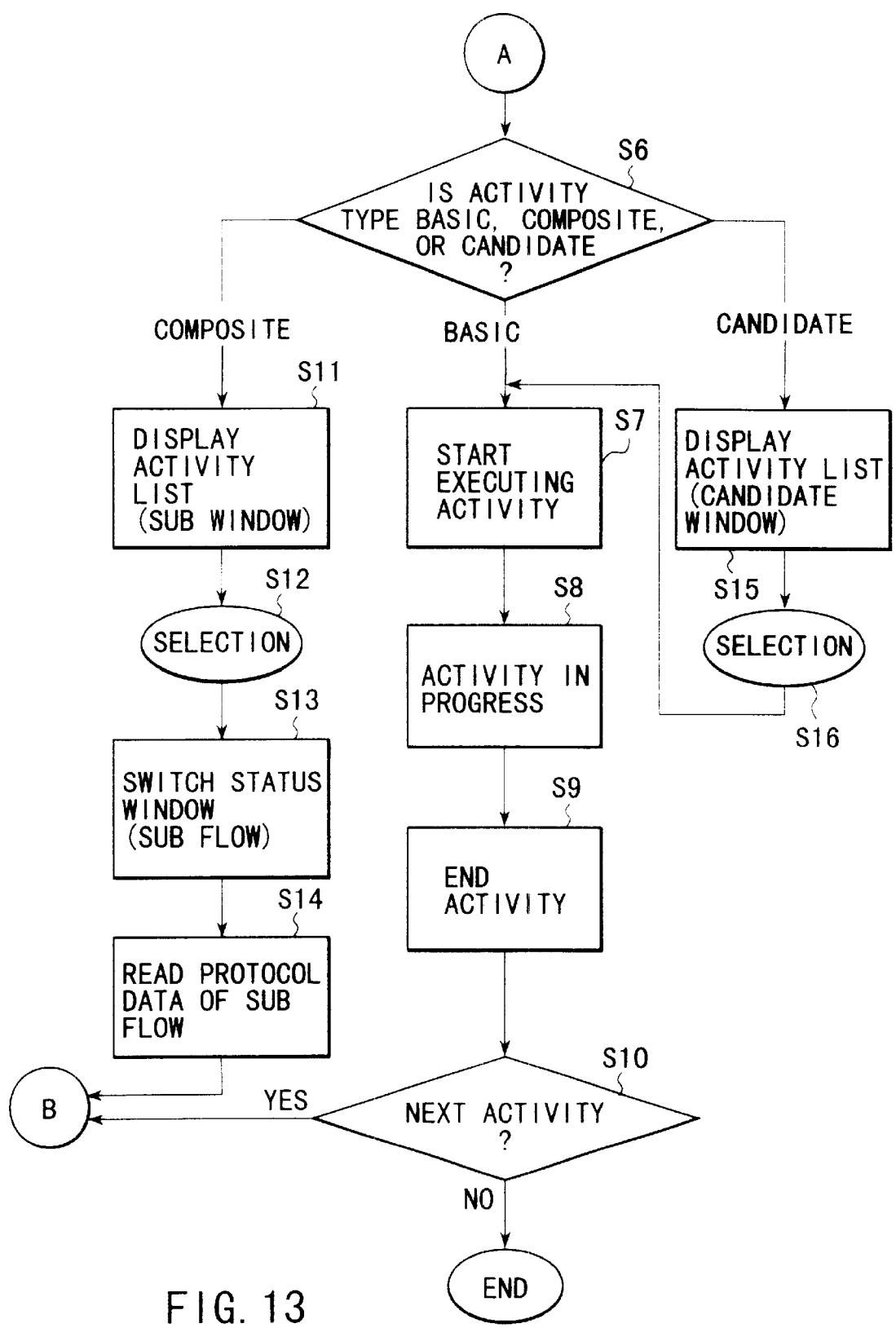
FIG. 13 is a flow chart for explaining the operation to be executed by the control section 22 when diagnosis progresses in accordance with the workflow 31.

FIG. 13 is a flow chart for explaining the operation to be executed by the control section 22 when the user progresses diagnosis in accordance with the workflow 31 shown in FIG. 5.

When reference to past images (activity "History") is ended, the operation advances to an activity corresponding to the next operation on the basis of selection of an activity "Scan" 40 by the user (or automatically). The workflow engine 223 determines the type of the next activity: "basic", "composite", or "candidate".

For example, when the "Scan" 40 is a basic activity, the operation of the control section 22 advances from step S6 to step S7. The workflow engine 223 starts the activity "Scan" 40 stored in the activity group storage section 225 (step S7).

After that, the activity "Scan" is executed. More specifically, the interior of the object is scanned with an ultrasonic wave through the ultrasonic probe to obtain a reception signal (step S8). When the scan operation is ended, the activity is also ended (step S9).

The workflow engine 223 determines whether the next activity is selected (step S10). If YES in step S10, the flow returns to step S5. If NO in step S10, the workflow system is terminated. In this case, since the diagnostic operation is based on the workflow 31, the user selects an activity "Measure" 42. The operation of the control section 22 returns to step S5 to display the status of "Measure". The operation advances to step S6 to determine the activity type.

For example, when the "Measure" 42 is a composite activity, the operation of the control section 22 advances from step S6 to step S11. The workflow engine 223 starts the "Measure" activity stored in the activity group storage section 225 (step S7).

When it is determined in step S6 that the activity "Measure" 42 is a composite activity, the flow advances to step S11 to display activities constructing the composite activity on the monitor 20 as a sub flow (step S11).

A sub flow means an operation procedure (flow) associated with a lower layer of a workflow. More specifically, a sub flow represents an operation procedure in which activities constructing a composite activity are arranged in a predetermined order.

Figure 14:
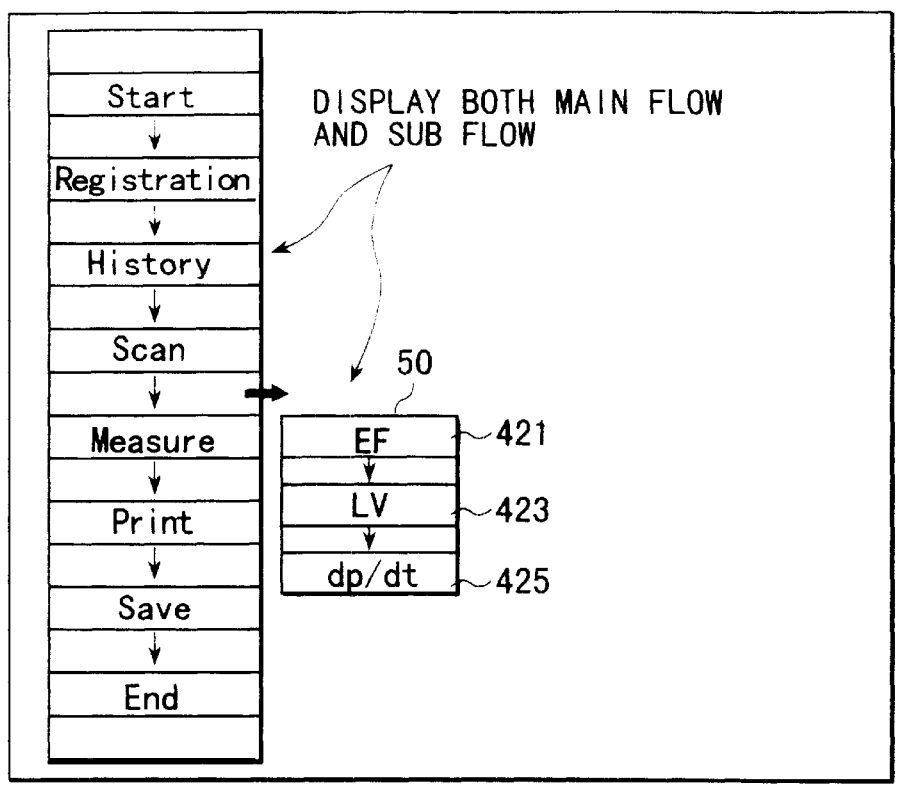
FIG. 14 is a view showing a window in which a sub flow 50 and the workflow 31 are simultaneously displayed.
Figure 15:
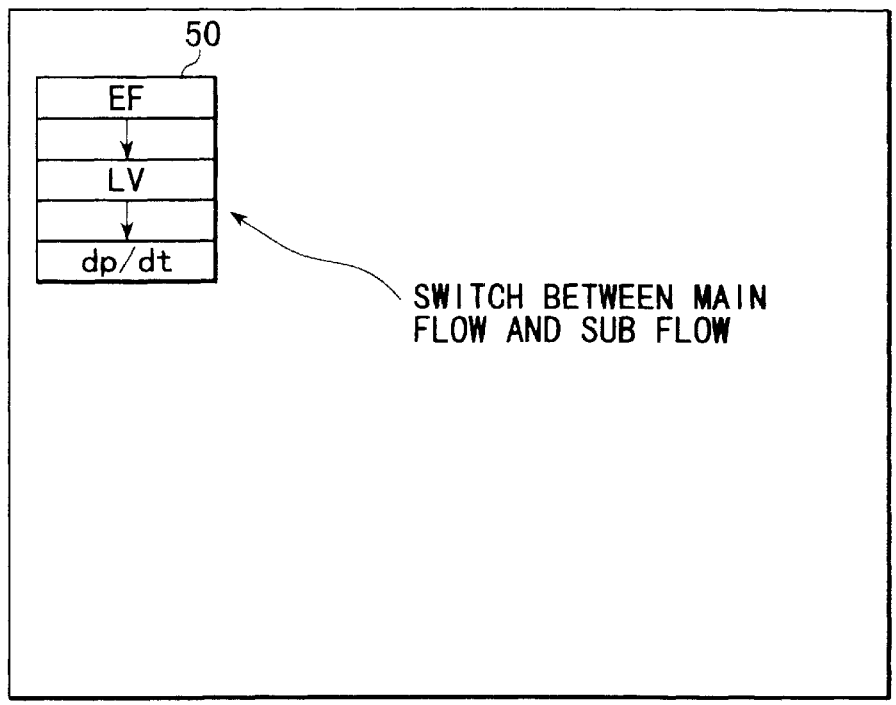
FIG. 15 is a view showing the sub flow 50 displayed in place of the workflow 31.

FIG. 14 shows a window in which a sub flow 50 containing activities constructing the composite activity and arranged in the operation order is displayed together with the workflow 31. In this case, the "Measure" 42 as a composite activity comprises basic activities "EF" for measuring the ejection fraction, "LV" for measuring the left ventricular volume, and "dp/dt" for measuring a change over time in left ventricular internal pressure. These activities are arranged in the order of operation and displayed in the sub flow 50 as symbols. This sub flow 50 may be displayed together with the workflow 31, as shown in FIG. 14. Alternatively, when a composite activity (in this case, the activity "Measure") in the workflow 31 is selected, the workflow 31 may be switched to the sub flow 50, as shown in FIG. 15. Switching display preferably allows discrimination between the workflow 31 and the sub flow 50 (for example, discrimination is done based on colors, or a title "sub flow" or the like is displayed).

If the sub flow has a composite activity, a new sub flow associated with the composite activity is hierarchically displayed.

According to this arrangement, activities constructing a composite activity can be displayed as a sub flow. Since the diagnostic operation can be executed in accordance with the sub flow, a complicated and diversified ultrasonic diagnostic apparatus can be easily operated.

Next, the workflow engine 223 determines whether the next activity is selected (step S10). If YES in step S10, the flow returns to step S5. If NO in step S10, the workflow system is terminated. Since this embodiment assumes diagnosis based on the workflow 31, the user selects an activity "Save" 46. The operation of the control section 22 returns to step S5 to display the status of the "Save" 46. The flow advances to step S6 to determine the activity type.

For example, when the "Save" 46 is a candidate activity, the operation of the control section 22 advances from step S6 to step S14. The workflow engine 223 starts a "Save" activity stored in the activity group storage section 225 (step S7).

If it is determined in step S6 that the activity "Save" 46 is a candidate activity, the flow advances to step S15 to display activities constructing the candidate activity on the monitor 20 as symbols in a candidate window (step S15).

Figure 16:
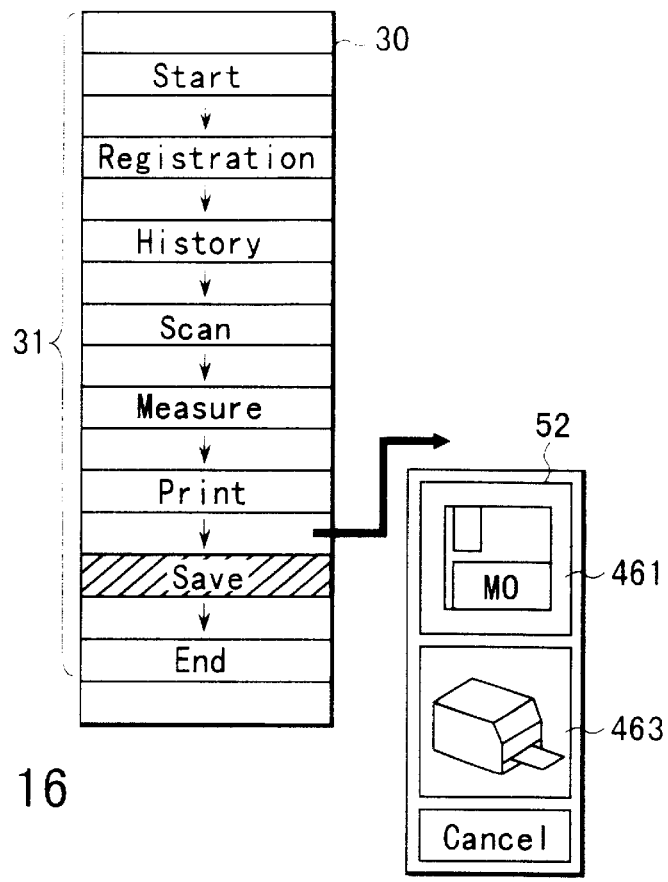
FIG. 16 is a view showing a candidate window 52 displayed on the monitor 20 when a candidate activity is selected.

FIG. 16 is a view showing a candidate window 52 displayed on the monitor 20 when the candidate activity "Save" 46 is selected. In the window 52, the symbols of basic activities "MO" 461 and "HD" 463 which construct the candidate activity "Save" are displayed.

When a desired activity (e.g., the "HD" 463) is selected from the candidate window 52 by user's manual operation (step S16), the workflow engine 223 reads out and executes the activity "HD" 463 stored in the activity group storage section 225 (step S7).

The activities are preferably arranged in descending order of use frequencies and displayed in the candidate window 52.

The activity "HD" 463 is executed (i.e., ultrasonic image data is stored in the HD). When storage is ended, the activity is also ended (step S9).

When the user selects the "End" activity, the workflow engine 223 terminates the workflow system.

An example of the basic operation of the workflow system has been described above. This workflow system also has various application functions. Several typical examples will be described below.

(1) An activity for executing various functions of the ultrasonic diagnostic apparatus associated with the diagnostic operation or a composite function constructed by various functions can be defined. The types of activities can be increased by inputting a new activity from an external input device (not shown). The user can insert an activity for executing a desired examination method or clinical application into the workflow protocol. Consequently, a diagnostic operation according to the degree of experience of the user can be performed using a workflow according to the protocol.

(2) A workflow protocol can be transmitted/received to/from another site through a network. This is effective when different hospitals want the same diagnostic operation.

Figure 17A:
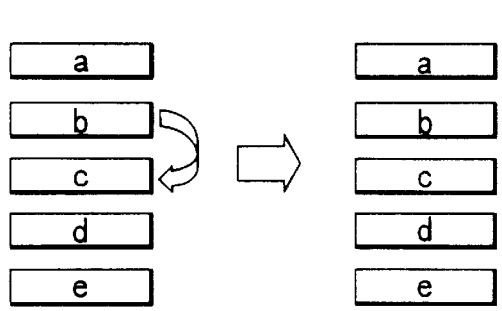
FIGS. 17A and 17B are views for explaining a change in display order of activities by operator's manual operation.

(3) The execution order of activities in the workflow is not a unique order according to the flow but can be changed. The execution order can be changed by two methods. As one method, the icons of activities to be changed are dragged and dropped to generate a new workflow in a desired order on the window of the monitor 20. Referring to FIG. 17A, b→c in the left workflow is changed to c→b as in the right workflow by this method.

Figure 17B:
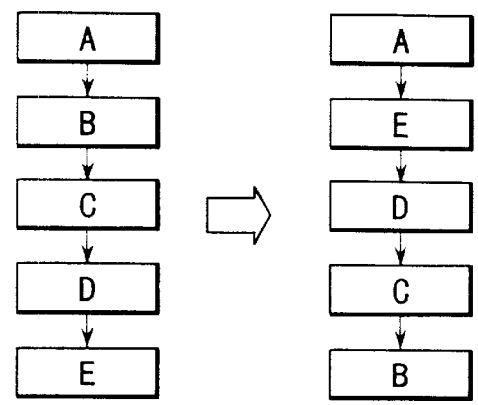

As the other method, the displayed workflow is kept unchanged, and the icons of activities are clicked in a desired order to manually execute the activities and change the order. At this time, the workflow displayed on the monitor 20 is preferably changed from the workflow displayed first (left side) to a new workflow (right side) in accordance with the order of manual execution, as shown in FIG. 17B.

Any change method can be executed at an arbitrary timing even during diagnosis according to a workflow. By any method, all operations can be executed without omission. This is because according to this workflow system, the icon of an executed activity can be discriminated from that of an unexecuted activity.

(4) A new activity can be inserted to an arbitrary portion of the workflow in progress. This function will be described later in more detail with reference to FIGS. 32 and 33.

Figure 48:
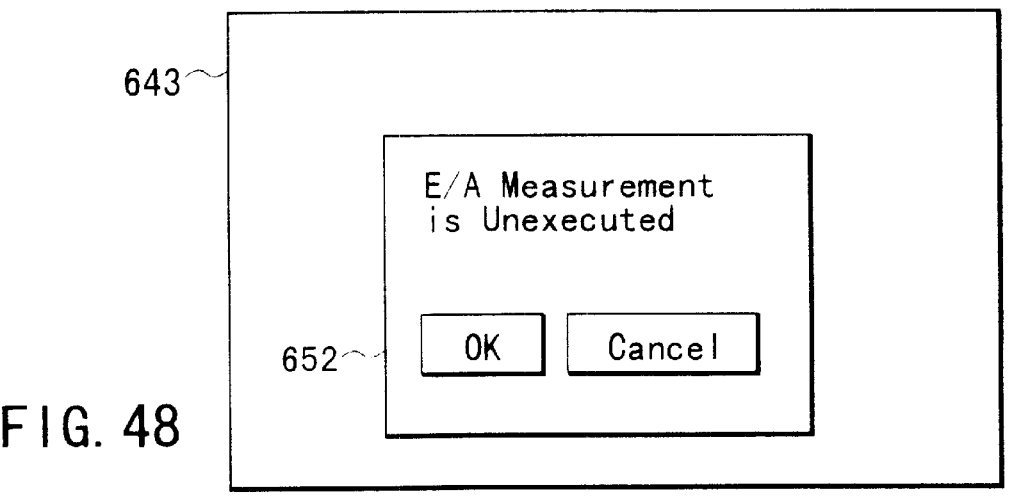
FIG. 48 is a view showing an example of window display representing caution or warning for an unexecuted item.
Figure 49:
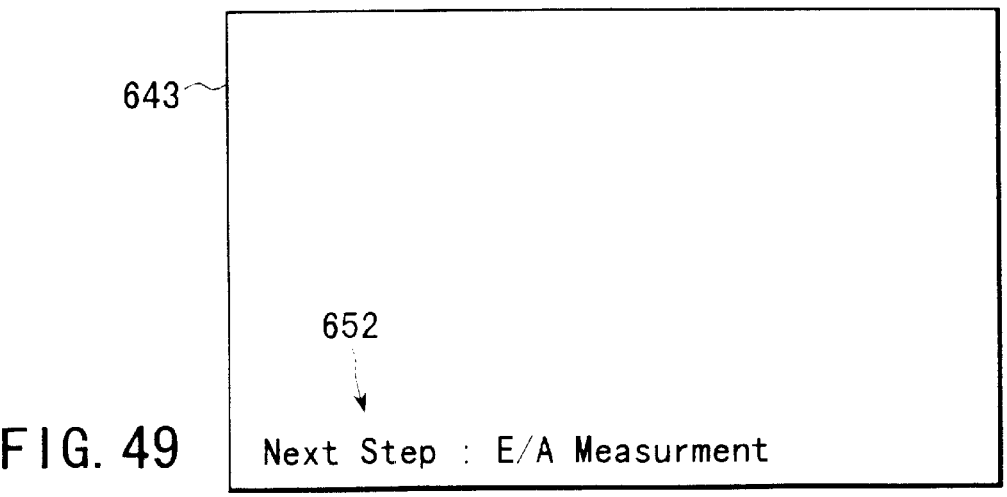
FIG. 49 is a view showing a display example of a second examination aid mode.

(5) An unnecessary activity in the workflow can be omitted. An activity in the workflow can be omitted by two methods. As one method, the icon of an activity to be omitted is deleted by a predetermined operation, a message is displayed, or the display form (shape or display color) of the activity is changed. AS the other method, the displayed workflow is kept unchanged, and the icon of an activity to be omitted is not clicked such that the activity is not executed. In the latter method, to confirm whether omission of the activity is intentional, the user should be cautioned or warned against the unexecuted activity by window display or the like at the end of workflow (FIG. 48).

According to the above-described arrangement, the following effects can be obtained.

A complicated and diversified ultrasonic diagnostic apparatus can be easily and appropriately operated. Additionally, an educational effect for an inexperienced user can be expected because the user can execute a diagnostic operation in accordance with a workflow.

Since optimum diagnosis can be executed without any wasteful operation, the operability can be improved. This is because an appropriate workflow is selected in accordance with a patient, disease, user, and the like. As another reason, when an activity program for realizing a desired function is stored in the activity group storage section 225, and a workflow protocol is defined, a workflow for aiding a desired diagnostic operation can be generated.

A more detailed operation procedure can be displayed, and an ultrasonic diagnostic apparatus can be easily and appropriately operated. This is because activities constructing a composite activity are displayed as a sub flow. As another reason, when an activity need be selected in the diagnostic operation, activities for realizing the operation are displayed in a candidate window.

The degree of freedom of diagnosis can be further increased, and the operability can be improved. This is because the arrangement of a workflow can be changed during execution of the workflow, and the workflow need not be restarted from the beginning.

Variations of a workflow will be described finally.

Figure 18:
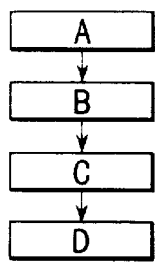
FIG. 18 is a view showing a workflow for sequentially executing the activities.

There are a variety of workflow types, although one workflow has been described above. More specifically, the workflow 31 shown in FIG. 5 has no interrupt processing and simply sequentially executes activities A, B, C, and D in this order, as shown in FIG. 18. However, a workflow system can also execute activities even in accordance with workflows in various forms to be described below.

Figure 19:
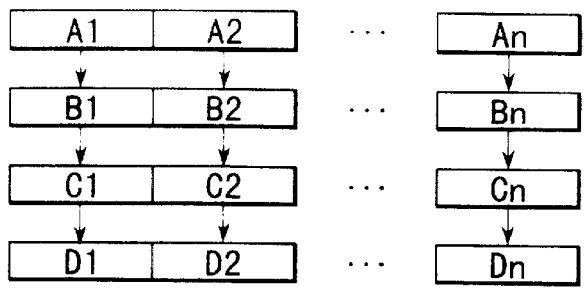
FIG. 19 is a view showing workflows for parallelly executing a plurality of activities.
Figure 20:
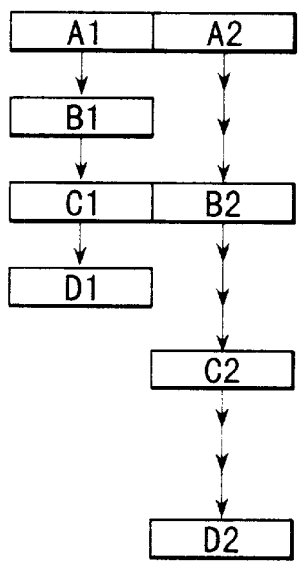
FIG. 20 is a view showing a workflow in which the foreground flow and background flow progress in independent times.

Referring to FIG. 19, n workflows are parallelly executed. The workflow types are discriminated by suffixes. To execute a plurality of workflows, workflow engines corresponding to the n workflows may be prepared in the control section 22 such that the first workflow is executed as a foreground flow while the (n−1) remaining workflows are simultaneously executed as background flows. One workflow engine may be used to alternately execute activities in the order of A1→A2 . . . →An→B1→B2 . . . →Bn as a foreground flow. The activities of the n workflows may be parallelly executed at random. If the workflows are to be simultaneously executed, the foreground flow and background flow may progress in independent times, as shown in FIG. 20. The workflows shown in FIG. 19 or 20 can be applied, for example, when rendering processing of image data acquired by a scan operation is executed as a background flow.

Figure 21A:
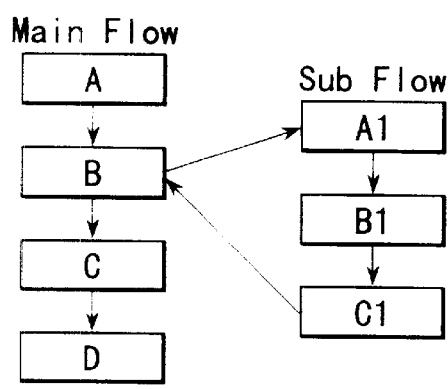
FIGS. 21A and 21B are views showing examples of workflows having shifts between the main flow and a sub flow.

FIG. 21A shows a workflow that shifts from the main flow to a sub flow. For a shift from the main flow to the sub flow, display is switched to the sub flow, or the main flow and sub flow are simultaneously displayed. For example, when a composite activity B is to be executed in FIG. 21A, the flow transits to the sub flow constructed by composite or basic activities A1, B1, and C1 (and simultaneously, display is switched to the sub flow). The activities A1, B1, and C1 are executed in this order in accordance with the sub flow. When the activity C1 is ended, the flow transits to the main flow (and simultaneously, display is switched to the main flow). The remaining operations C and D are executed in this order in accordance with the main flow. This example shown in FIG. 21A corresponds to the relationship between the sub flow 50 and the workflow 31 in the composite activity "Measure" shown in FIGS. 14 and 15.

Figure 21B:
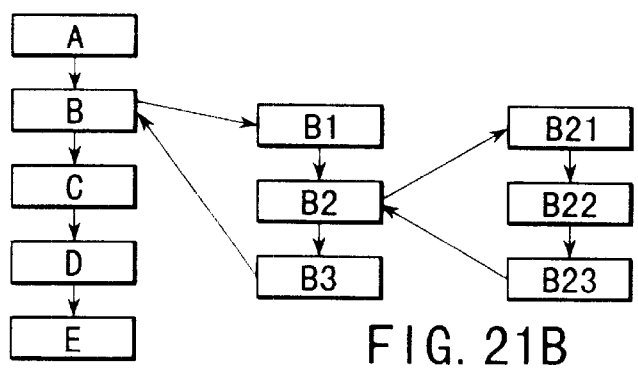

FIG. 21B shows a case wherein when a sub flow has a composite activity, the flow shifts from the sub flow to a lower sub flow. A number of sub flows can be displayed in correspondence with composite activities. When a workflow has a hierarchical structure with a plurality of layers, the flows of all layers including the main flow can be simultaneously displayed. However, this display form may increase the workflow display region and narrow the ultrasonic image display region on the screen. Hence, only a sub flow is preferably displayed. It is important to display the sub flow while clarifying its hierarchical position.

Figure 22:
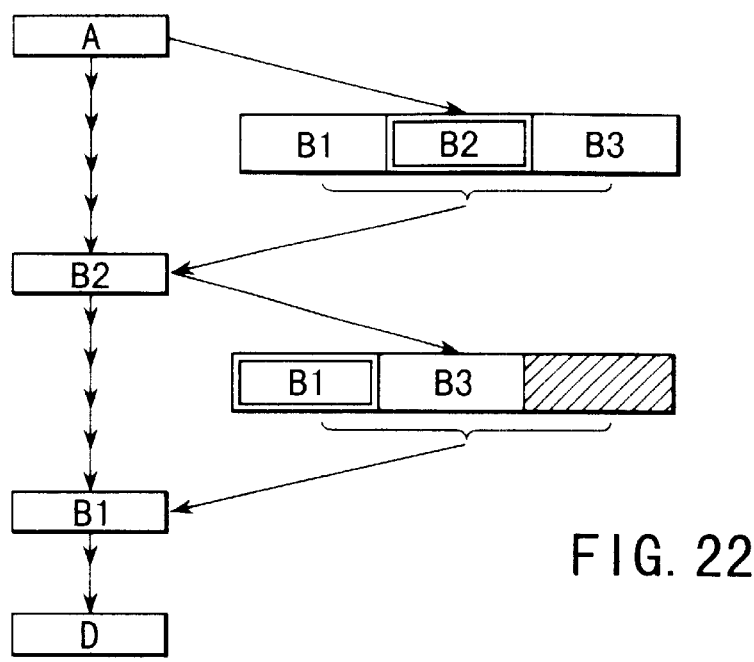
FIG. 22 is a view showing a selected candidate window which does not display an activity B2.

FIG. 22 shows an example of a workflow having a plurality of branched activities (three activities B1, B2, and B3 in FIG. 22) next to the activity A. In this workflow, the activities B1, B2, and B3 are functions corresponding to operations to be executed, respectively, and executable in an arbitrary order. In this case, a flow having the icons of the activities B1, B2, and B3 parallelly displayed is branched from the main flow. The activities B1, B2, and B3 are inserted into the main flow in accordance with the order of selection/execution. The display form of the icon of an executed activity is automatically discriminated on the basis of the display priority or whether the activity has been executed. Referring to FIG. 22, the activity B2 is selected first from the activities B1, B2, and B3. The activity B2 is not displayed in the subsequent parallel icon display, and the icons of the activities B1 and B3 are parallelly displayed.

Figure 23A:
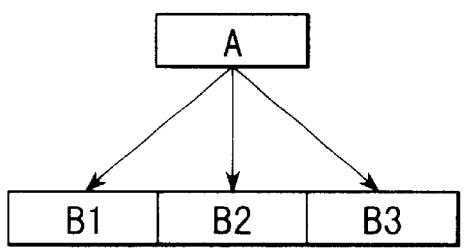
FIG. 23A is a view showing a workflow in which activities B1, B2, and B3 are present as candidate activities to be selected next to an activity A.
Figure 23B:
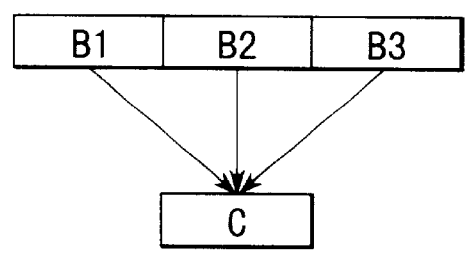
FIG. 23B is a view showing a workflow in which the flow advances to an activity C when one of a plurality of activities is executed.

FIG. 23A shows another example of a workflow having a plurality of branched activities (activities B1, B2, and B3 in FIG. 23A) next to the activity A. FIG. 23B shows an example of a workflow having a plurality of branched activities (three activities B1, B2, and B3 in FIG. 23B) before the activity C. According to these workflows, for example, two operation procedures can be defined.

As one operation procedure, a workflow in which the flow can advance to the next operation when any one of the plurality of branched activities is executed can be defined. Referring to FIGS. 23A and 23B, the workflow defines a procedure in which the operation advances from the activity A to any one of the activities B1, B2, and B3, and after execution of the selected activity, the operation advances to the activity C. In this case, the workflow can be regarded to define one symbolic activity containing all the activities B1, B2, and B3, in which any one of the activities B1, B2, and B3 is selected. The activities B1, B2, and B3 correspond to the above-described candidate activities. Referring to FIG. 16, the status window of the activities B1, B2, and B3 as selection candidates is called a candidate window.

The other operation procedure can be defined as a workflow in which the flow cannot advance to the next operation unless all activities are executed. Referring to FIGS. 23A and 23B, the workflow defines a procedure in which after execution of the activity A, all the activities B1, B2, and B3 are executed in an arbitrary or predetermined order, and only when this condition is satisfied, the flow can advance to the activity C (this method can also be regarded as a modification to the workflow shown in FIG. 22).

Figure 24A:
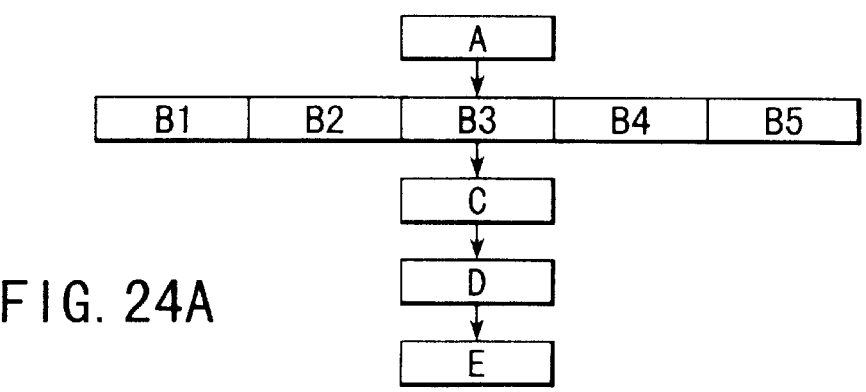
FIGS. 24A, 24B, and 24C are views showing workflows having a plurality of activities to be branched.

FIG. 24A shows a still another example of a workflow having a plurality of branched activities (five activities B1, B2, B3, B4, and B5 in FIG. 24A). The above two operation procedures will be described on the basis of this workflow.

A case wherein the workflow shown in FIG. 24A defines the former operation procedure will be described first. In this case, when a selected one of the plurality of activities B1, B2, B3, B4, and B5 is executed, the flow can advance to the next activity C.

A case wherein the workflow shown in FIG. 24A defines the latter operation procedure will be described next. In this case, when all of the plurality of activities B1, B2, B3, B4, and B5 are executed, the flow can advance to the next activity C. However, arbitrariness is preferably ensured such that the flow can be forcibly advanced to the next operation by a predetermined operation without executing all the activities.

Application examples of the workflow defining the former operation procedure will be described with reference to FIGS. 24B and 24C.

Figure 24B:
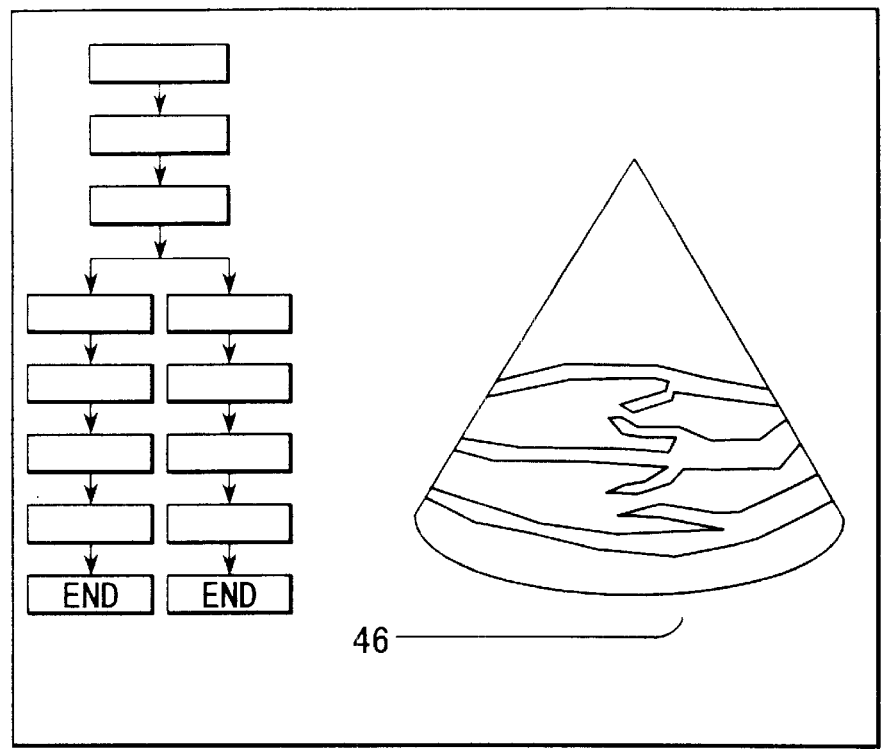
Figure 24C:
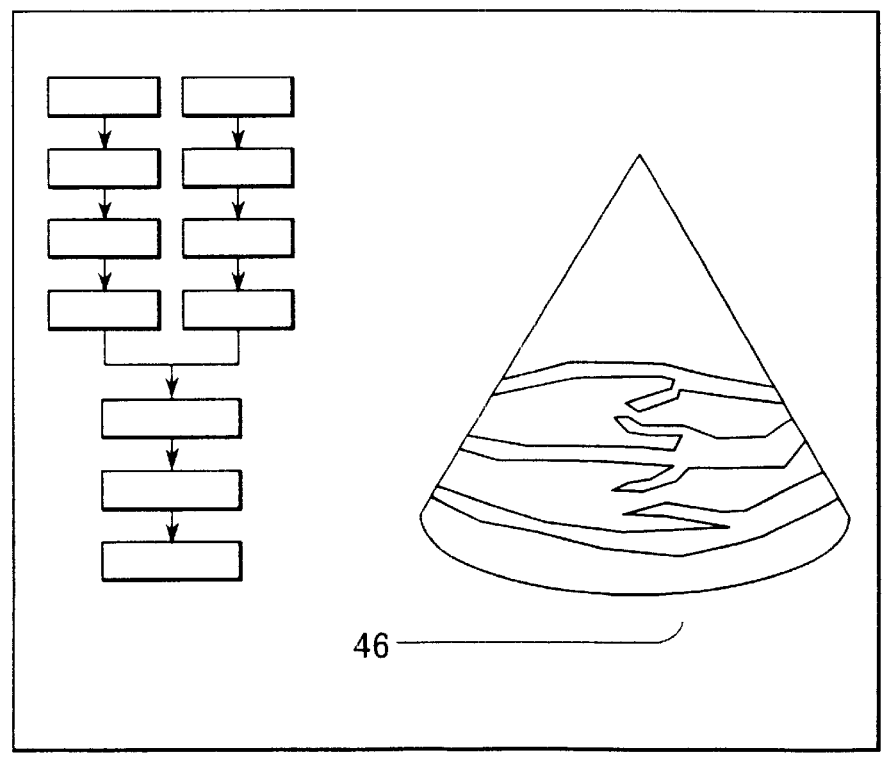

FIG. 24B shows an example in which a plurality of workflows branched from one workflow are parallelly displayed. FIG. 24C shows an example in which a plurality of branched workflows that are parallelly displayed merge to one workflow. Referring to FIGS. 24A and 24B, the activities A, B1, B2, and C are executed in accordance with the operation procedures as defined above.

When a workflow contains branches as selection candidates (i.e., in the above-described latter workflow), the selection operation can be automatically performed by defining candidate activities. An example will be described below with reference to FIGS. 25 to 28.

Figure 25:
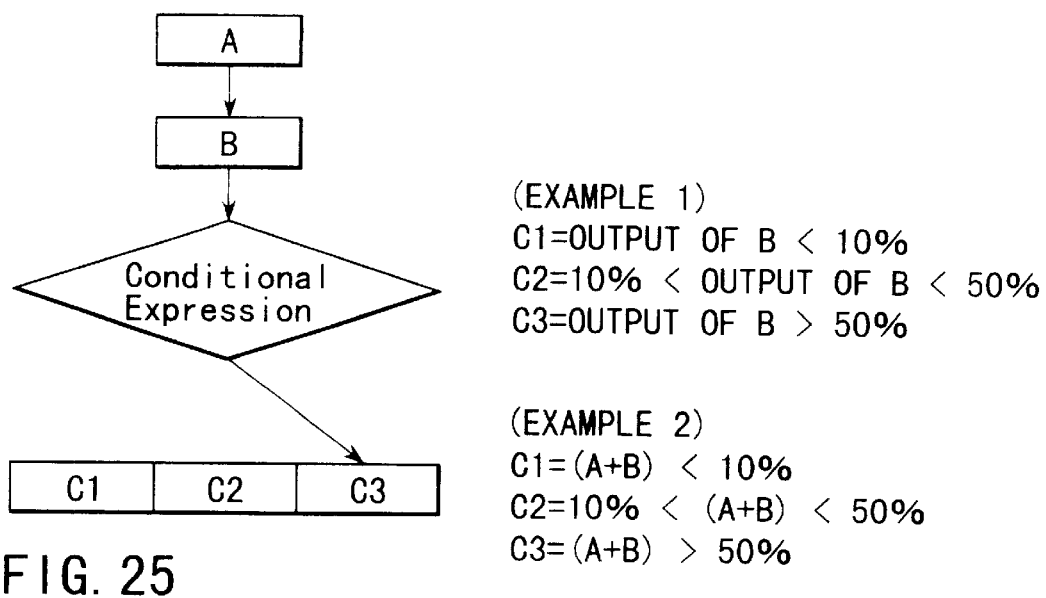
FIG. 25 is a view showing a workflow for automatically selecting a candidate activity on the basis of conditional expressions.

FIG. 25 shows an example in which a candidate activity is automatically selected on the basis of conditional expressions. This can be realized by setting an activity for substituting a measurement result into predetermined conditional expressions, performing desired calculations, and selecting a candidate activity on the basis of the calculated values. For example, an activity may be set in which an EF value is measured by circulatory system measurement, and the next measurement activity is determined depending on whether the measurement result is 10% or less, 10% to 50%, or 50% or more.

Figure 26:
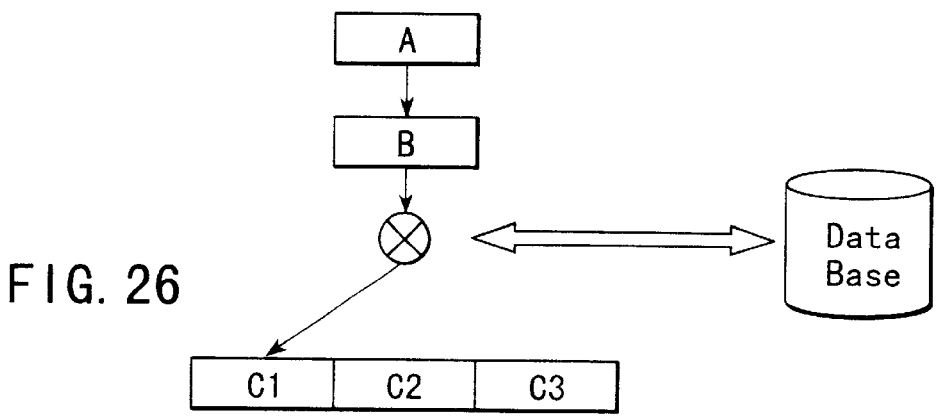
FIG. 26 is a view showing a workflow for automatically selecting a candidate activity by looking up a database.

FIG. 26 shows an example in which a candidate activity is automatically selected by looking up a database. This can be realized by setting an activity for transferring a measurement result as basic information to a database in which pieces of information are registered in advance, searching for a corresponding result, and automatically selecting a candidate activity on the basis of the search result. According to the workflow containing this activity, a plurality of pieces of basic information can be processed, and an optimum result can be searched for by composite search.

Figure 27:
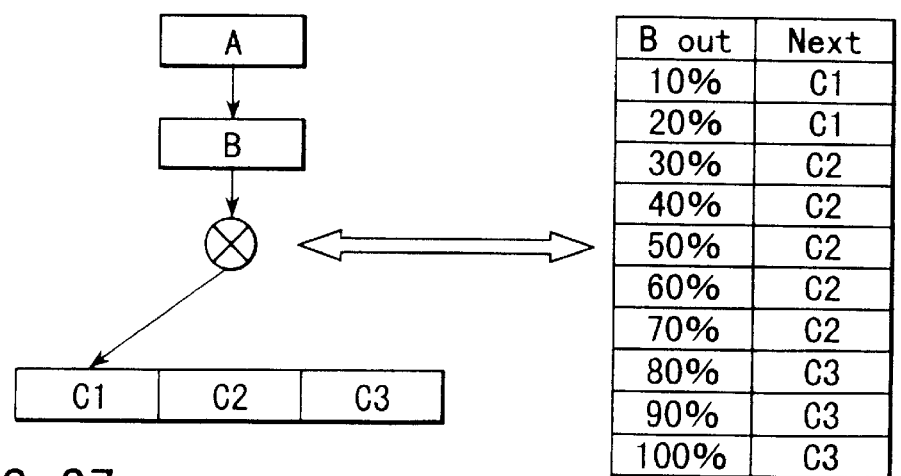
FIG. 27 is a view showing a workflow having an activity for looking up a table instead of the database shown in FIG. 26.

FIG. 27 shows a workflow having an activity for looking up a table instead of the database shown in FIG. 26. This activity can be relatively easily set as compared to the activity for constructing a database.

Figure 28:
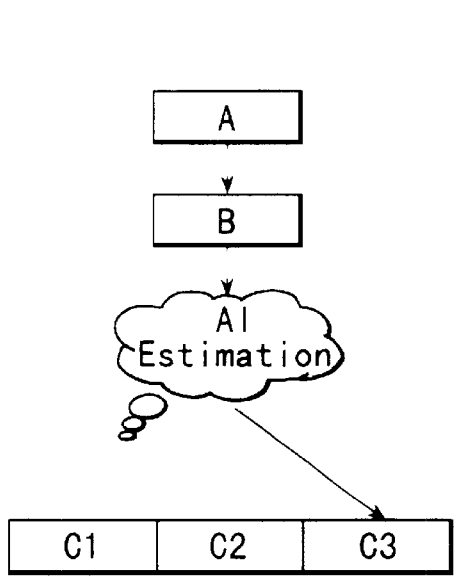
FIG. 28 is a view showing a workflow having an activity for selecting a candidate activity using an estimation algorithm such as A1.

FIG. 28 shows a workflow having an activity for selecting a candidate activity using an estimation algorithm such as AI (Artificial Intelligence).

Figure 29:
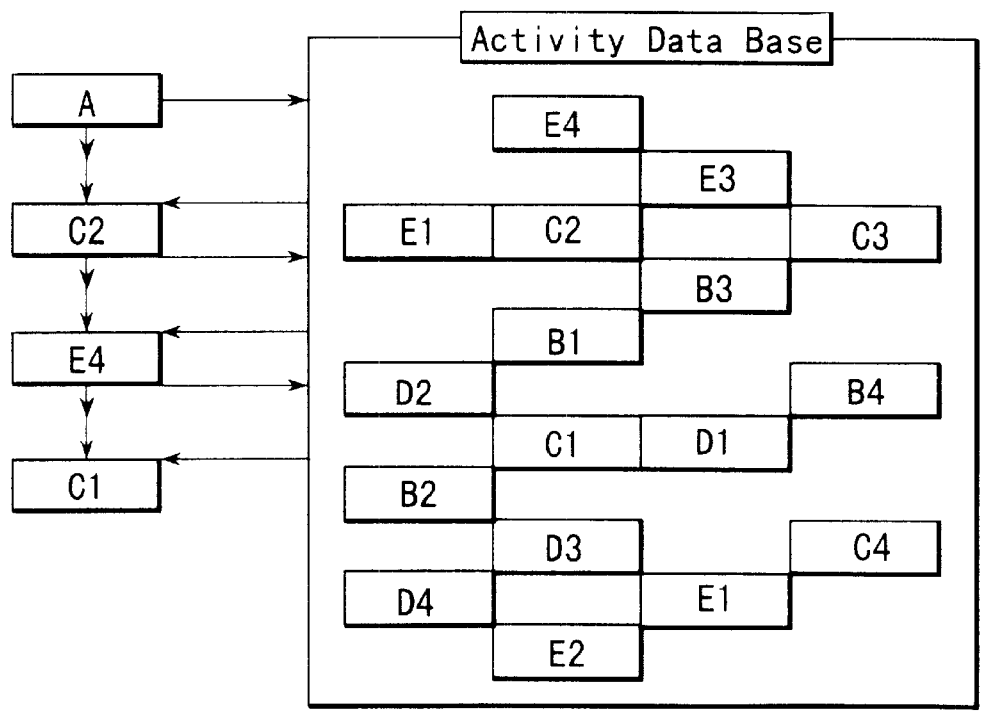
FIG. 29 is a view showing a workflow for selecting a candidate activity by an activity having an auction function.

FIG. 29 shows a workflow for selecting a candidate activity by an activity having an auction function. This activity constructs a workflow by repeating a series of operations. For example, when an operation according to the activity A is ended, information obtained by this operation is input to an activity database. In the database, an optimum activity is determined in accordance with the information. In this example, an activity C2 is determined and executed. When the activity C2 is ended, information is input to the database again, and the next optimum activity is determined. This example can be applied to a case wherein the next activity is not determined in advance in a workflow which is being executed.

Figure 30:
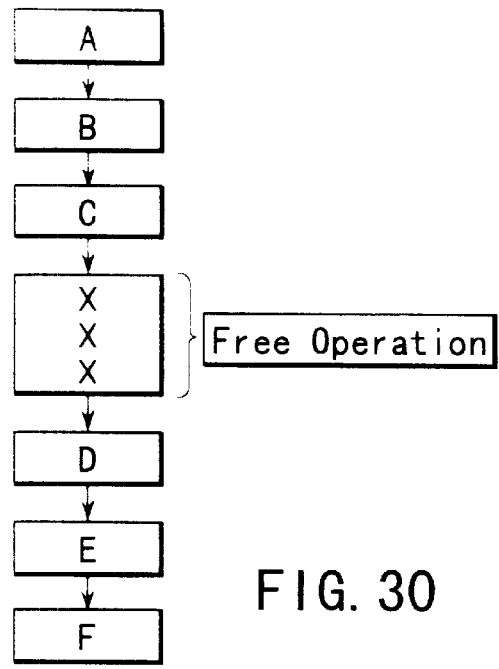
FIG. 30 is a view showing a workflow which assumes insertion of a new activity by an interrupt operation for a workflow protocol from the beginning.

FIG. 30 shows a workflow which assumes insertion of a new activity by an interrupt operation for a workflow protocol from the beginning. According to this workflow, activities can be freely set and executed by manual operation at a portion "Free Operation" in the workflow. When registration of the workflow newly set by manual operation is enabled, the same workflow can be executed for the next time without setting activities by manual operation.

Figure 31:
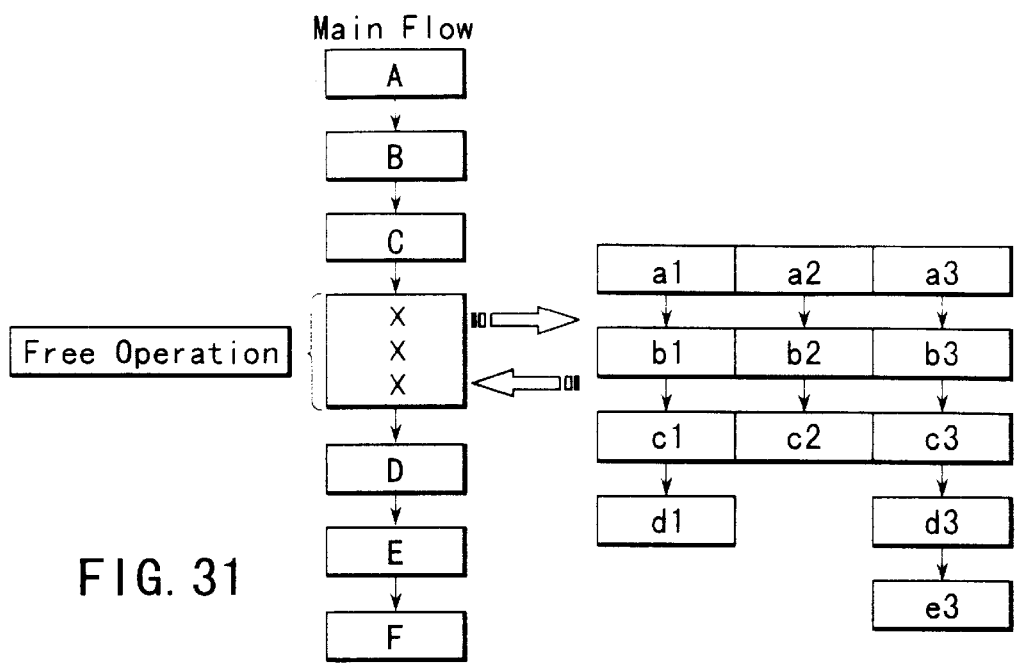
FIG. 31 is a view showing a workflow capable of appropriately executing only an independent sub flow during the manual operation as an application of the workflow shown in FIG. 30.

FIG. 31 shows an application of the workflow shown in FIG. 30. This workflow can appropriately execute only an independent sub flow during manual operation.

A workflow which defines an operation procedure for inserting a new activity into a workflow in progress will be described next.

Figure 32:
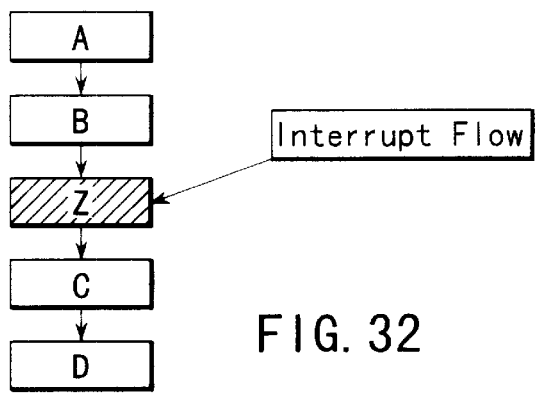
FIGS. 32 and 33 are views showing a workflow which allows insertion of another undefined control into a workflow in progress.

FIG. 32 shows a workflow for inserting, to an arbitrary position, an activity which is undefined in a workflow protocol in progress by an interrupt. To do this interrupt, a desired position in the workflow displayed on the screen of the monitor 20 is selected (for example, when arrows indicating the progress direction of the workflow are displayed, an arrow at a position where an activity is to be inserted is selected, and if no arrows are displayed, a position between the icons of activities is selected), and an addition button for adding a new activity is pressed. With this operation, a list of activities that can be added to the selected position (procedure) is displayed. The user only need select an activity to be added by an interrupt.

Figure 33:
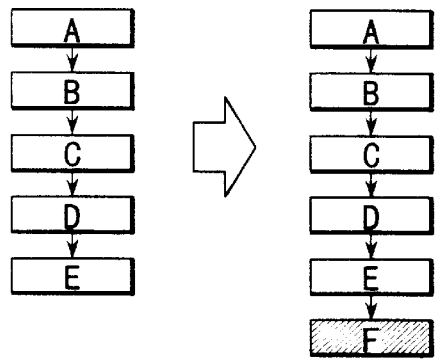

FIG. 33 shows an example in which a new activity is added to the end of a workflow. Referring to FIG. 33, one activity is added. However, a plurality of activities or a new workflow may be added.

The workflow newly generated by an interrupt can preferably be registered. In this case, all activities need not always be registered because their necessities change in units of activities that can be realized by the apparatus. For example, a criterion may be set to register only activities of levels which are so important that a history must be recorded as examination procedures.

The above-described activity insertion is also possible when the workflow protocol displayed on the monitor 20 is being executed. Hence, the degree of freedom diagnosis can be increased, and the operability can be improved. This is because the workflow in progress need not be stopped, the redefined workflow need not be restarted, and an interrupt can be done at an arbitrary timing.

Figure 34:
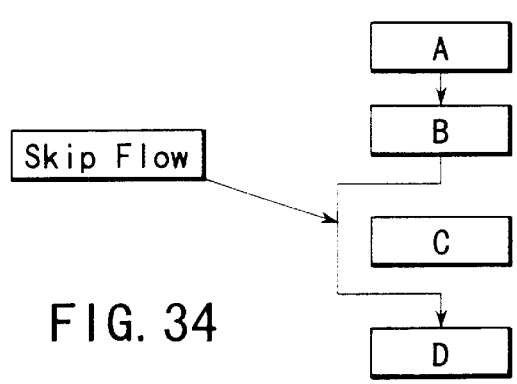
FIG. 34 is a view showing an example of a workflow with a change in operation procedure.

FIG. 34 shows an example of a workflow in which activities are not always sequentially executed, and if necessary, the operation is started from an arbitrary position by skip or re-execution. This example is effective when only a specific examination or measurement need be re-executed.

Figure 35:
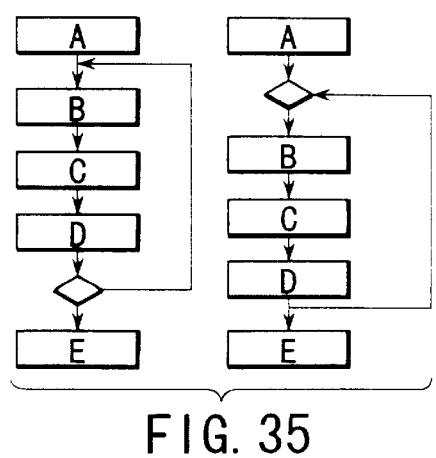
FIG. 35 is a view showing a workflow including a loop.

FIG. 35 shows a workflow including a loop operation. According to this workflow, an operation procedure for repeating a series of flows constructed by a plurality of activities under a predetermined condition can be defined.

Even by the above-described various workflows, a complicated and diversified ultrasonic diagnostic apparatus can be easily and appropriately operated.

Second Embodiment

In the second embodiment, the editing function of an ultrasonic diagnostic apparatus according to the present invention will be described. The editing function can be roughly classified into two functions.

One is a first editing function for a workflow protocol. In the first embodiment, a workflow protocol that is defined and stored in advance is read out, and diagnosis is performed on the basis of a workflow defined by the workflow protocol. In the second embodiment, however, a new workflow protocol is manually set. The first editing function is used for this manual setting.

The other is a second editing function for a specific function (activity). A function of generating a diagnostic record (to be referred to as a "Report" in the following description) will be exemplified.

First two representative examples of workflow protocol definition using the first editing function will be described first.

FIG. 36 shows the first example of a protocol editing sheet 80 used to manually set a workflow protocol. The sheet 80 is displayed on a monitor 20 when a workflow protocol editing operation is started by a predetermined operation.

In this example of the protocol editing sheet 80, workflow protocols are classified in units of users. Hence, the protocol editing sheet 80 has items "user name", "workflow name", and "workflow protocol".

In the item "user name", a user name is registered. In the item "workflow name", an arbitrary name is assigned to a new workflow protocol to be edited. In the item "workflow protocol", the workflow protocol is edited.

A workflow protocol can be edited using the protocol editing sheet by, e.g., the following method.

First, a user name and workflow name are registered. Activities corresponding to operations for realizing desired diagnosis are registered in the item "workflow protocol" in accordance with the operation order, thereby editing a new workflow protocol. The new workflow protocol edited in the above way is stored in a protocol database 234. This workflow protocol is set as a workflow, for example, when the user logs in to the ultrasonic diagnostic apparatus (simultaneously, a status window associated with the workflow is displayed on the monitor 20). Hence, the user can execute diagnosis according to a desired operation procedure.

Referring to FIG. 36, the workflow protocol of a "Normal" workflow that is executed by Dr. A as a standard operation is defined by activities shown on the uppermost line of FIG. 36. To the contrary, the workflow protocol of a "Normal" workflow on the lowermost line of FIG. 36, which is executed by Dr. G as a standard operation, does not have a "Refer Previous Image" activity (activity corresponding to a symbol "History" in a workflow 31).

That is, even for standard ultrasonic diagnosis which is to be normally executed, the operation procedure may change depending on the user (doctor in this case), and accordingly, the types and order of activities to be started may also change. According to the ultrasonic diagnostic apparatus of the present invention, desired workflow protocols and workflows can be defined and registered in units of users. For this reason, each user can easily execute diagnosis in accordance with a desired procedure. The workflow protocols may be manually set and registered on the basis of diseases to be diagnosed, patients, charges for diagnosis, and medical associations.

To define an activity "Measure" as a composite activity, a sub flow managed by another window can preferably be set as needed after the main flow is set.

According to this arrangement, workflow protocols having desired contents can be set in accordance with various standards. As a consequence, the operability can be improved, and the ultrasonic diagnostic apparatus can be easily and appropriately operated.

The above-described first example assumes that activities to be registered in the item "workflow protocol" are stored in an activity group storage section 225 in advance. However, when an activity for realizing a desired function is newly defined and stored in the activity group storage section 225, desired functions of all ultrasonic diagnostic apparatuses can be freely inserted into workflow protocols.

In the second example to be described below, the user defines and inserts an activity to edit a workflow protocol.

Referring to FIG. 36, "diagnosis A", "diagnosis B", and "diagnosis C" inserted into the workflow of Dr. H are composite activities constructed by newly defining a series of examination routines ordinarily executed by Dr. H. More specifically, for example, the composite activities "diagnosis A", "diagnosis B", and "diagnosis C" are functions respectively corresponding to different series of operation procedures; an ultrasonic image is sensed in a predetermined sensing mode, measurement necessary for the diagnosis is performed, and the diagnostic result or finding is displayed.

Figure 37:
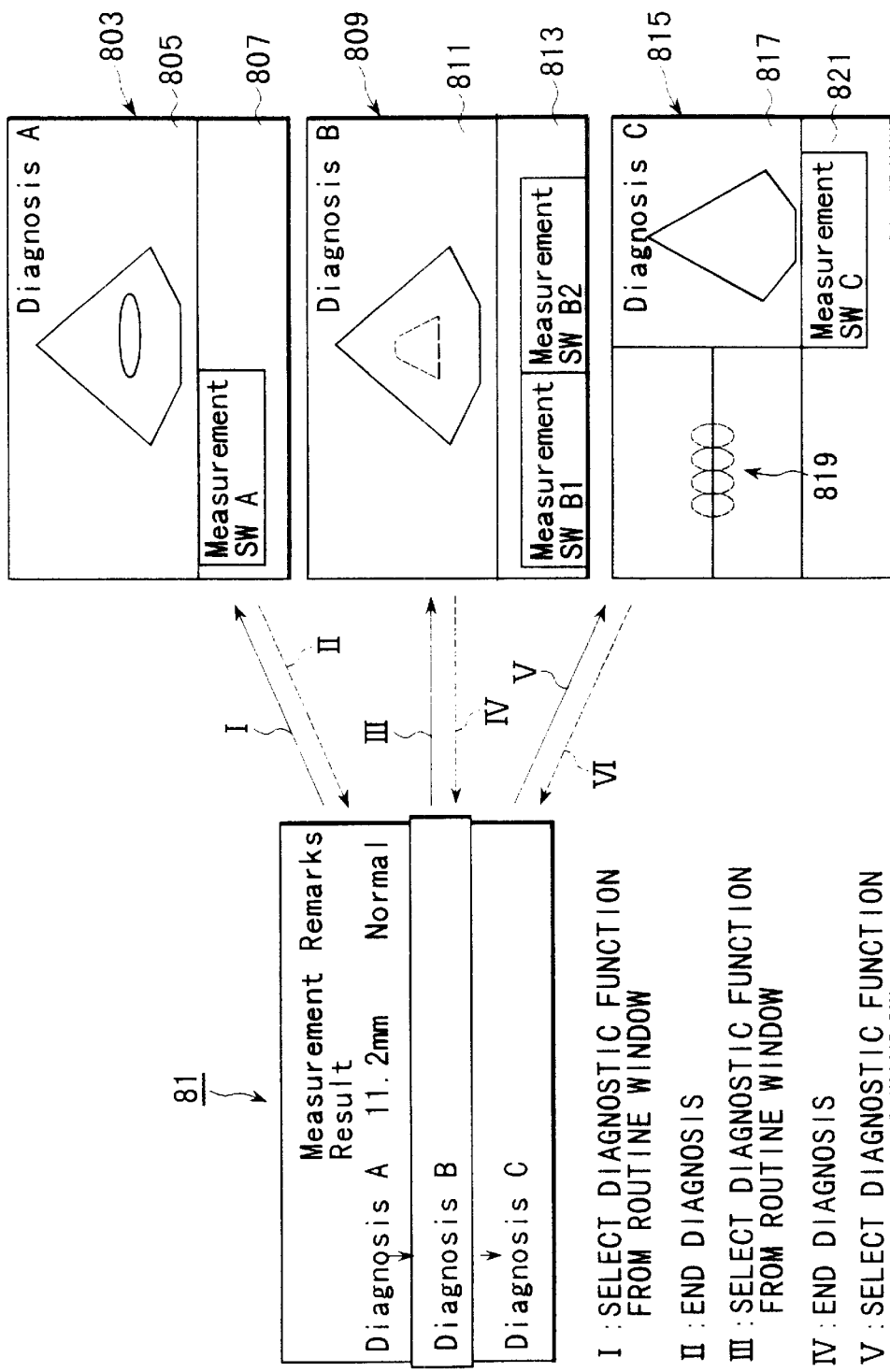
FIG. 37 is a view showing examples of windows displayed on the monitor when an ultrasonographic routine is executed.

As has been described in the first embodiment, a registration operation and the like are sequentially executed in accordance with a workflow, and then the diagnostic operation is started. At this time, for example, an ultrasonographic workflow 801 corresponding to an ultrasonographic routine as shown in FIG. 37 is displayed on the monitor 20. In this case, as shown by the workflow protocol in FIG. 36, the ultrasonographic routine is constructed by three diagnostic operations A to C.

Assume that to perform diagnosis A, the user selects the activity "diagnosis A" from the status window of the workflow 801 on the monitor 20 shown in FIG. 37. The window on the monitor 20 is changed to a window 803 associated with the diagnosis A (I). In the window 803, an ultrasonic tomographic image 805 obtained by ultrasonic scanning in a sensing mode defined in advance is displayed.

At the same time, an operation panel 807 associated with the diagnosis A is displayed, e.g., at the lower portion of the monitor 20 or on a TCS (Touch Command Screen). The operation panel 807 associated with the diagnosis A has, e.g., a measurement switch A necessary and essential for the diagnosis A.

The measurement operation in the diagnosis A is executed by selecting the measurement switch A. When only the switch associated with measurement necessary and essential for the diagnosis A is displayed, undesired skip of measurement, or execution of another measurement function or unwanted ultrasonic scanning can be prevented.

The measurement result is stored in an external storage device 25 (FIG. 1) as ultrasonographic data of diagnosis A together with the ultrasonic tomographic image 805 obtained by the diagnosis A.

When measurement is ended, display on the monitor 20 returns to the status window of a workflow 81 (II). The measurement result obtained by the diagnosis A and finding and remarks associated with the diagnosis A are displayed. Not only the measurement result, finding, and remarks but also another data or data unique to the object can be displayed as needed.

To perform diagnosis B, the user selects the activity "diagnosis B" from the status window of the workflow 81 on the monitor 20. Display on the monitor 20 is changed to a window 809 for the diagnosis B (III). In the changed window 809 associated with the diagnosis B, an ultrasonic tomographic image 811 obtained by ultrasonic scanning in a sensing mode defined in advance is displayed.

At the same time, an operation panel 813 associated with the diagnosis B is displayed, e.g., at the lower portion of the monitor 20 or on a TCS. The operation panel 813 associated with the diagnosis B has, e.g., measurement switches B1 and B2 necessary and essential for the diagnosis B.

The measurement operation in the diagnosis B is executed by selecting the measurement switches B1 and B2. When only the switches B1 and B2 associated with measurement necessary and essential for the diagnosis B are displayed, necessary and sufficient measurement can be performed without undesired skip of measurement, or execution of another measurement function or unwanted ultrasonic scanning. The measurement result is stored in the external storage device 25 as ultrasonographic data of diagnosis B together with the ultrasonic tomographic image 811 obtained by the diagnosis B.

The diagnostic operation is similarly performed for diagnosis C (IV). An ultrasonic tomographic image 817 (B-mode display) and ultrasonic tomographic image 819 (spectrum display) of the diagnosis C and an operation panel 821 of the diagnosis C are displayed in a window 815 of the diagnosis C (V).

After the series of diagnostic operations are performed, display on the monitor 20 returns to the status window of the workflow 81 (VI). The measurement result obtained by the diagnosis C and finding and remarks associated with the diagnosis C are displayed. The image data and measurement data obtained by the diagnosis A to C are stored in the external storage device 25.

In the above description, all examination routines of the diagnosis A to C are executed. However, an unnecessary examination routine can be omitted, or the order of execution can be changed, as needed.

After the above-described diagnostic operations, the diagnostic procedure advances to the "Report" generation operation (FIG. 36).

According to this arrangement, workflow protocols having desired contents can be set in accordance with various standards. As a consequence, the operability can be improved, and the ultrasonic diagnostic apparatus can be easily and appropriately operated.

According to this arrangement, an ultrasonic image diagnostic apparatus with high use efficiency and operability can be provided. This is because operation procedures according to the degree of experiences and use contents can be defined in units of users.

The second editing function will be described next by exemplifying the function "Report" of generating a diagnostic record.

When the flow advances to the next operation in accordance with a workflow, a workflow engine 223 reads out the activity "Report" from the activity group storage section 225 and activates the activity. This activity "Report" is also defined by the user in advance to realize the following function.

Figure 38:
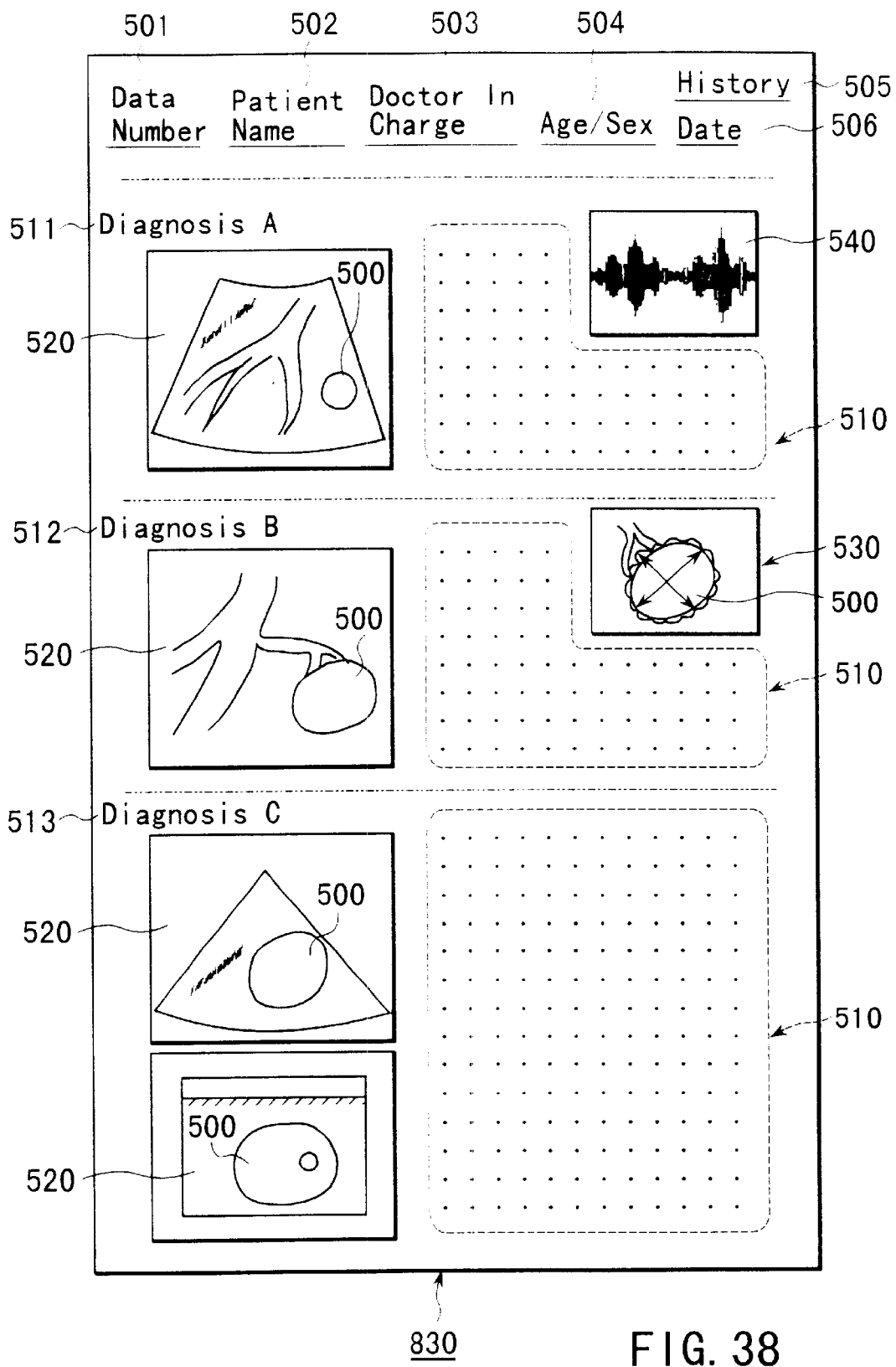
FIG. 38 is a view showing an example of an ultrasonic diagnostic record 830.

FIG. 38 shows an example of the ultrasonic diagnostic record 830 generated upon executing the activity "Report".

The displayed contents of the ultrasonic diagnostic record 830 will be described first.

The ultrasonic diagnostic record 830 is a report that reflects the results of the above examination routines. As for the contents, an examination data number 501, patient name 502, doctor name 503, patient age/sex 504, generation date 506, and change history 505 are displayed as basic information. As diagnostic information, data 511 of the diagnosis A, data 512 of the diagnosis B, and data 513 of the diagnosis C are displayed in different regions in accordance with the order of the examination routines. The contents of the pieces of diagnostic information will be described below.

As the data 511 of the diagnosis A, image data 520, Doppler measurement data 540, and diagnostic finding 510 are displayed. The image data 520 contains a target diagnosis portion 500. The types of data of the diagnosis A to be displayed can be freely changed to another types of data selected by the user as needed. Changed data is not limited to data stored in the external storage device 25. Instead, image data externally input to the ultrasonic image diagnostic apparatus may be selected.

In the data 512 of the diagnosis B, the image data 520 is displayed, as in the data of the diagnosis A. A window in which the size of the target diagnosis portion 500 is measured is displayed in a measurement window 530. For the data of the diagnosis B as well, image data or measurement data necessary for the diagnosis can be exchanged, as in the diagnosis A.

This also applies to the data 513 of the diagnosis C. The diagnostic finding 510 is input by the user such as a doctor in charge or an ultrasonographic technician.

The ultrasonic diagnostic apparatus according to the present invention has an editing function associated with the ultrasonic diagnostic record 830. This editing function will be described next.

The format of the ultrasonic diagnostic record 830 will be described first. The format of the ultrasonic diagnostic record 830 shown in FIG. 37 has already been input to the apparatus. Various data are laid out at positions on a predetermined format and output. However, the present invention is not limited to this, and the format of the ultrasonic diagnostic record 830 can be arbitrarily changed. To do this, a predetermined format of the ultrasonic diagnostic record 830 only need be input to the apparatus or generated on the apparatus.

Data described in the ultrasonic diagnostic record 830 will be described next. Data to be inserted to the ultrasonic diagnostic record 830 can be arbitrarily changed. As described in the first embodiment, each data stored in the external storage device 25 has an identifier such as a patient ID or date. The user can set desired contents by designating the identifier of data to be inserted to the ultrasonic diagnostic record 830. Additionally, necessary data can be read out at an arbitrary timing, or arbitrary data can be searched using a keyword.

Some variations of the ultrasonic diagnostic record 830 will be described below.

(1) The ultrasonic diagnostic record 830 can be used not only as an examination record but also as, e.g., a clinical chart. In this case, after an input of necessary finding, the doctor in charge should input an ID number or the like to protect the contents of the clinical chart. This holds security and prevents alteration.

(2) In addition, for example, only the data 513 of the diagnosis C can be output in combination with information such as the examination data number 501, patient name 502, doctor name 503, patient age/sex 504, change history 505, or generation date 506 for identifying the patient. The user can also arbitrarily omit an item which need not be displayed, enlarge specific image data, or delete unnecessary data.

(3) The above-described editing of the ultrasonic diagnostic record 830 can be performed by, e.g., operation on the monitor 20. Alternatively, only data may be sent to a separate computer and edited.

(4) The workflow protocol edited in the above way and the ultrasonic diagnostic record 83 can be transmitted/received between sites through a network. This function is effective, for example, when information in respect of a patient is exchanged between different hospitals.

According to the above-described arrangement, labor in examination data classification operation can be reduced. This is because the result of a series of ultrasonographic routines, which has a desired format and contents for the ultrasonic diagnostic record 830, can be output by an output device 90 or the like without requiring artificial labor.

Third Embodiment

In the first embodiment, an ultrasonic diagnostic apparatus which displays a workflow as a status window and notifies a user of the operation procedure to improve the operability has been described. In the third embodiment, an ultrasonic diagnostic apparatus having not only this function but also a function (to be referred to as a help function hereinafter) of displaying a comment about a disease using an anatomical view, a representative example of an ultrasonic image, or a description about a diagnostic operation performed by starting each activity will be described.

The help function can be executed by selecting a help button provided at a predetermined position, e.g., the lowermost portion of a status window 30, as needed, to cause a workflow engine 223 to start a help activity from an activity group storage section 225.

That is, if the workflow system is being activated, desired help information is preferably extracted at an arbitrary timing. This can be realized by activating the above-described help activity at a desired timing.

The help activity is normally executed by an interrupt operation. For example, when the help button is selected (i.e., the help activity is activated) in a diagnostic operation according to a workflow 31, an interrupt according to the workflow shown in FIG. 32 is performed.

Figure 39:
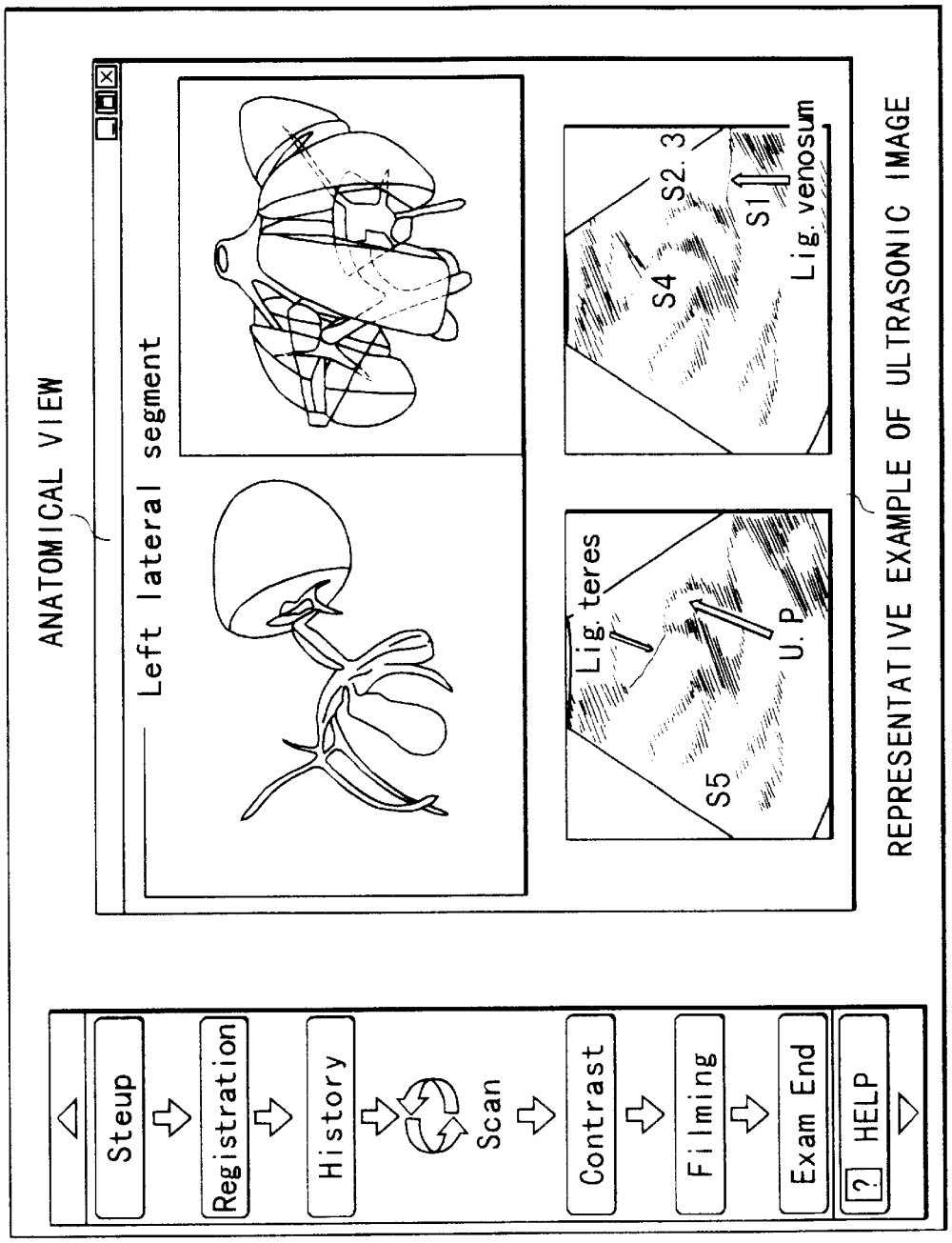
FIG. 39 is a view showing a help window that is displayed on the monitor 20 by a help function to show examples of anatomical views and ultrasonic images.

As an example of a comment by the help function, when, e.g., "MI" (Myocardial Infarction) is registered in a disease name item 342 of a registration sheet 34 shown in FIG. 4, and the help button is selected, help data associated with myocardial infarction are selected, and anatomical views or ultrasonic image examples are displayed as comments about myocardial infarction, as shown in FIG. 39. In diagnosing a patient of myocardial infarction (i.e., when "MI" is registered in the registration sheet 34), when the help button is selected during activating an activity associated with "Scan", help data associated with "myocardial infarction" and "Scan" are selected, and appropriate use examples of an ultrasonic probe for diagnosis of myocardial infarction are displayed.

Figure 40B:
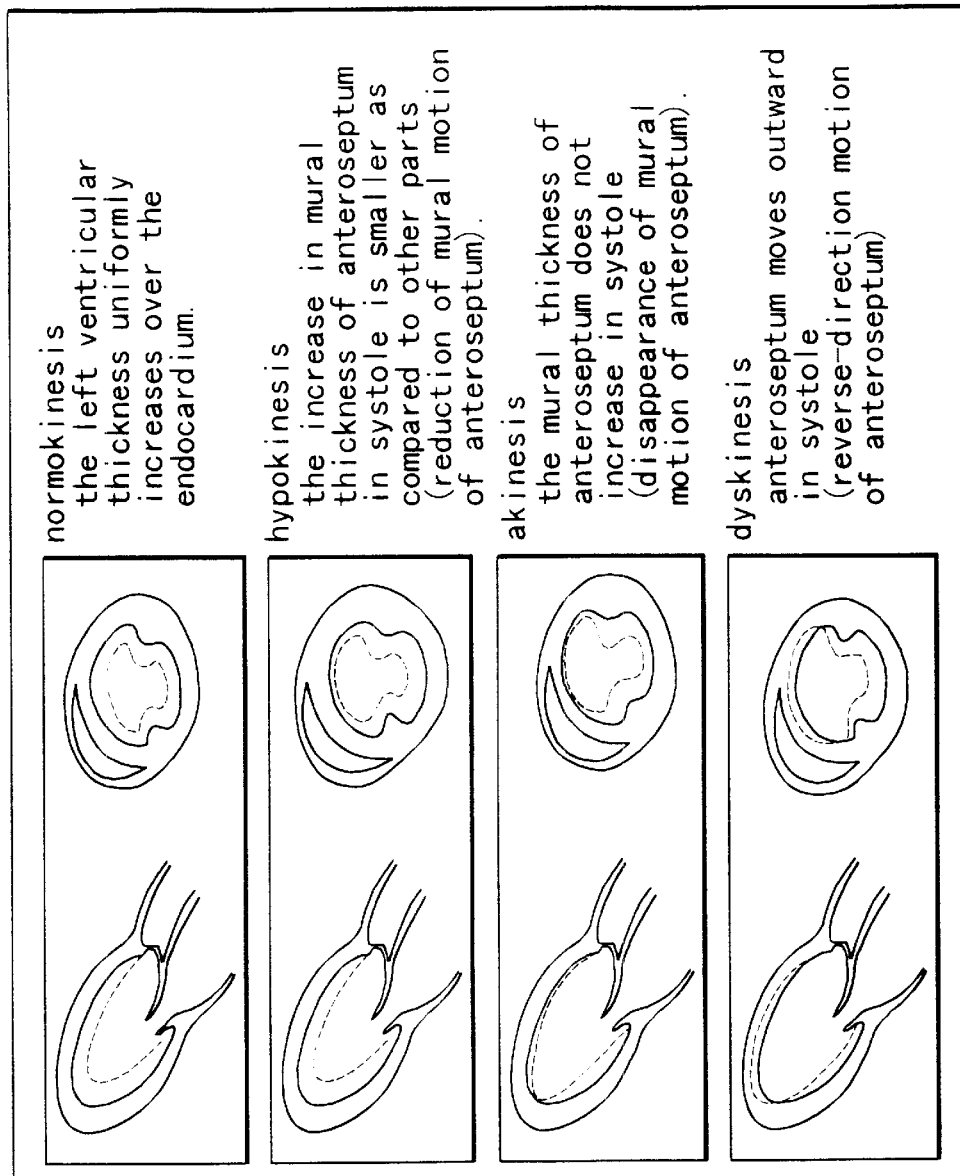
FIGS. 40A and 40B are views showing an example of comments displayed on the monitor 20 when an activity associated with "Measure" is executed in diagnosing a patient of myocardial infarction.
Figure 40A:
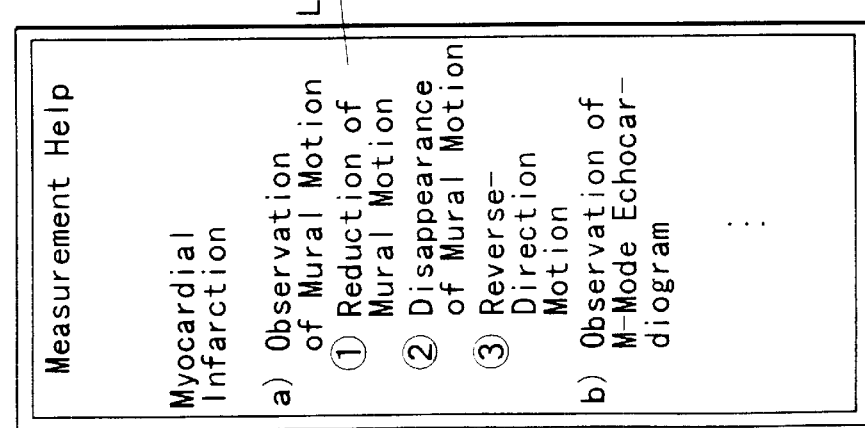

FIGS. 40A and 40B show examples of comments displayed on a monitor 20 by the help function when an activity associated with "Measure" is being activated for diagnosis of a patient of myocardial infarction. FIG. 40A shows a window which displays information such as the image observation method and measurement method for myocardial infarction as help contents. FIG. 40B shows a window which hierarchically displays more detailed comment contents by a selection operation of, e.g., clicking the pointer on an item of the help contents displayed in FIG. 40A. When an item of the help contents is selected, an activity corresponding to the item can preferably be directly started. This can be realized by linking the operation of clicking an item of the displayed help contents to the start of a corresponding activity.

According to this arrangement, the operability can be further improved.

Comments displayed by the help function include the manual of the apparatus, examination method, and a description of a clinical application, as needed, in addition to the above-described anatomical view, ultrasonic image example, image observation method, and measurement method.

According to this arrangement, aid information associated with diagnosis can be provided by displaying an anatomical view of a diagnosis object or a sample image of an ultrasonographic image, as needed, during a diagnostic operation according to a workflow or sub flow. As a result, even inexperienced user can execute appropriate diagnosis. Especially, for an inexperienced user, aid for the diagnostic operation can be obtained, and an educational effect can also be expected.

Fourth Embodiment

In the fourth embodiment, an operation of checking a result of diagnosis executed in accordance with a workflow will be described. A check function based on two viewpoints, i.e., a function of checking whether a workflow has been appropriate (i.e., whether no operation has been skipped in the operation procedure) and comparing a measurement value with a general data value (for example, for a specific disease, a measurement value is compared with a normal value or sample value associated with a predetermined disease) will be described below.

This check function can be executed by causing a workflow engine 223 to start an activity for performing the following check operation from an activity group storage section 225.

Figures 41, 42:
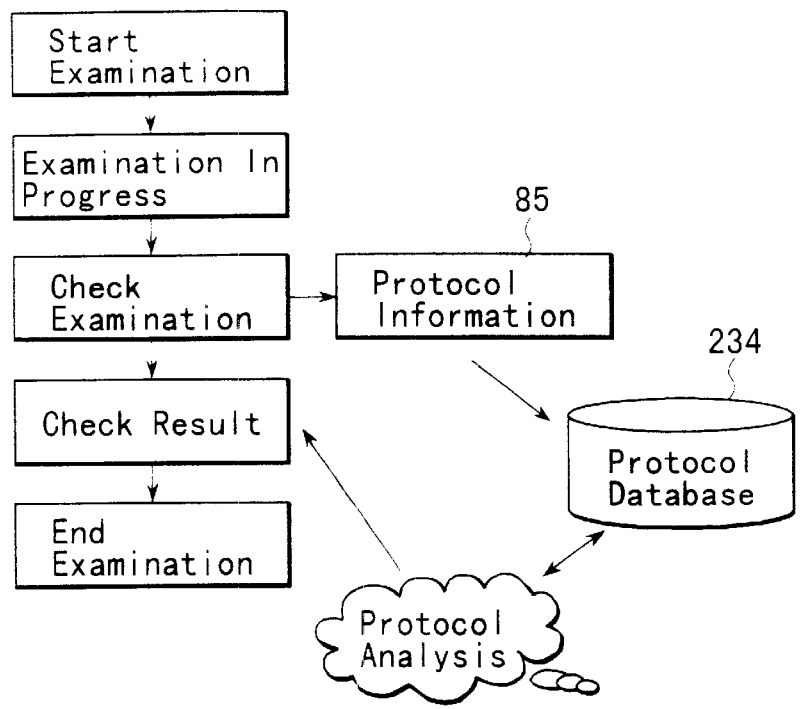
FIG. 41 is a view for explaining a mechanism for automatically checking contents of an examination.
FIG. 42 is a view showing a protocol check sheet 90.

FIG. 41 is a view for explaining a mechanism for automatically checking contents of an examination.

The user starts an activity to be described below at the end of an examination (for example, when "Save" in a workflow 31 is ended). This operation may be an interrupt operation shown in FIG. 32 or 33 by a predetermined operation. Alternatively, the workflow may contain the check activity in advance.

The check activity executes, e.g., the following function. The workflow engine 223 starts the check activity to input workflow protocol information executed for the current examination to a protocol database 234. The workflow engine 223 executes a protocol analysis routine for comparing many workflow protocols which have already been registered in the database 234 with the data of the workflow protocol executed for the current examination, thereby mechanically examining the propriety of the procedure and disease. The workflow engine 223 also executes a measurement result analysis routine for comparing a sample value associated with a predetermined disease stored in advance with the measurement result, thereby mechanically examining the propriety of the measurement result.

For example, assume a case wherein the propriety of the contents of an examination is to be examined after the end of a series of examination operations. To improve the examination quality, the workflow protocol used for the examination is compared with the protocol used for the standard examination of myocardial infarction. By executing this comparison, the difference from standard data can be easily confirmed, and it can be checked whether an unexecuted operation is present. If a necessary but unexecuted operation is present, the examination is filled up by executing this operation, so a more reliable diagnostic result can be obtained.

FIG. 42 shows a protocol check sheet 90 used to check the propriety of the result of comparison between the standard workflow protocol and the executed workflow protocol, and the measurement result.

The protocol check sheet 90 has protocol check items 901 for checking the workflow protocol and measurement result check items 903 for checking the propriety of measurement values. For the protocol check items 901, a standard workflow protocol associated with a predetermined disease, which is stored in the protocol database 234, is displayed in a protocol column 905. An executed operation (activity) has a check mark. In the measurement result check items 903, measurement values by the executed operations (activities) are displayed. If comparison with a normal value range stored in advance reveals that the measurement value is not normal, the measurement value is displayed in, e.g., a different color. If an incredible value is displayed due to an measurement error, warning is preferably done by display or sound.

Assume that there is a suspicion of myocardial infarction after the end of the series of examination operations.

FIG. 43 shows a diagnosis check sheet 93 used to check the propriety of diagnosis on the basis of the measurement result.

The diagnosis check sheet 93 has a diagnostic finding input 930 for registering a disease to be diagnosed (myocardial infarction in FIG. 39), diagnostic items 931 to be diagnosed on the basis of a measurement value, diagnostic result items 933 associated with the diagnostic items 931, disease data items 935 representing general data of the diagnostic items 931 associated with the disease input to the diagnostic finding input 930, and comments 937 representing comments for comparison between the diagnostic result items 933 and the disease data items 935.

On the basis of diagnosis executed in accordance with the workflow 31, the diagnostic results of the diagnostic items 931 associated with myocardial infarction are displayed in the diagnostic result items 933. In addition, general data of the diagnostic items 931 associated with myocardial infarction are displayed in the disease data items 935. The workflow engine 223 executes the measurement result analysis routine for comparing the general data with the measurement results and displays "re-measurement required" or the like as evaluation of the measurement results in the comments 937. At this time, a measurement value obtained by measurement or a standard value based on general data may be simultaneously displayed in the diagnostic result item 933 and disease data item 935, respectively.

For an examination performed by the user as an interrupt operation, the above-described check function can be executed at an arbitrary timing by starting the check activity by manual operation. This result can preferably be looked up anytime as a report.

According to this arrangement, even when diagnosis based on a measurement result is difficult (for example, a symptom associated with a predetermined disease is just appearing, and it is doubtful that the patient has the disease), more reliable diagnosis can be executed using the function of checking the propriety of the diagnostic operation, measurement result, or diagnostic result. Especially, for an inexperienced user, aid for the diagnostic operation can be obtained, and an educational effect can also be expected.

Fifth Embodiment

In the fifth embodiment, another example of an ultrasonic diagnostic apparatus which can be easily operated by either a skilled person or a beginner in accordance with the degree of experience of the operator and realize accurate diagnosis will be described.

Figure 44:
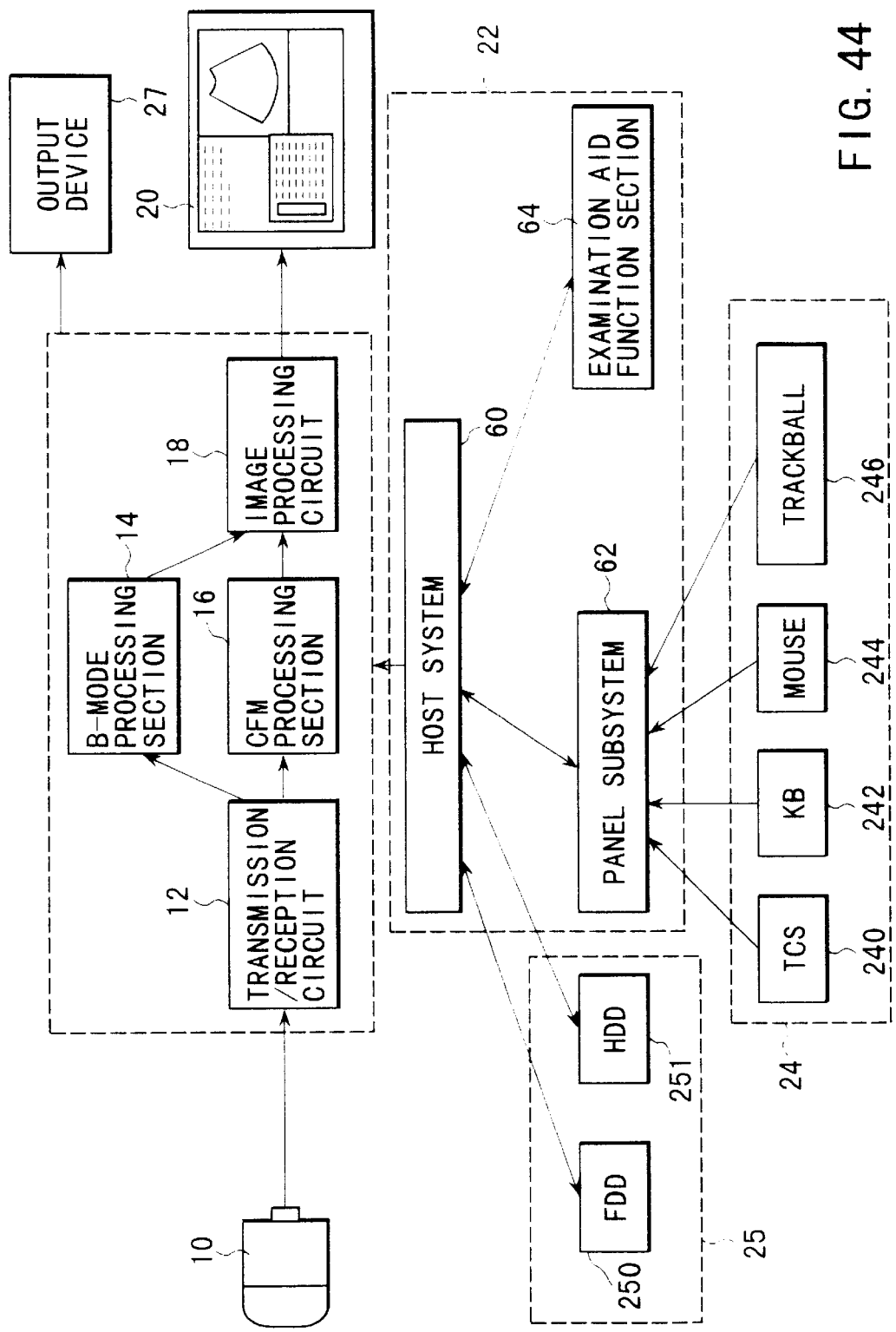
FIG. 44 is a block diagram showing the schematic arrangement of an ultrasonic diagnostic apparatus according to the fifth embodiment.

FIG. 44 is a block diagram showing the schematic arrangement of this ultrasonic diagnostic apparatus according. The same reference numerals as in FIG. 1 denote the same elements in FIG. 44, and a detailed description thereof will be omitted. Only new elements will be described.

A control section 22 has a host system 60, panel subsystem 62, and examination aid function section 64. These elements will be described below.

The host system 60 has a means for obtaining vital measurement information on the basis of an obtained ultrasonic diagnostic image. Information obtained by measuring each ultrasonic diagnostic image is useful as auxiliary information for diagnosis. Examples of such information are structural dimensions of a living body for a B-mode image, the amount of a change over time in structural dimensions of a living body for an M-mode image, and a physical amount such as velocity or acceleration of a living body or blood flow velocity in a living body for a Doppler-mode image. These measurement values are used to calculate indices for vital evaluation in terms of measurement, function, or quality (for example, measurement values of an inner diameter and mural thickness can be obtained by measuring an M-mode image of a left ventricle in diagnosing a circulatory system). These measurement values are used to calculate indices for evaluating the cardiac function such as the left ventricular volume or ejection fraction.

The panel subsystem 62 is a means for processing various operations from the operator, including an instruction operation associated with execution of data acquisition and image measurement and an operation of inputting/editing examination specifying information and examination item information. The panel subsystem 62 is connected to a TCS (Touch Command Screen) 240, KB (KeyBoard) 242, mouse 244, and trackball 246 of an input section 24.

The examination aid function section 64 is associated with a feature point of the present invention. The examination aid function section 64 has two functions of aiding execution of an examination by the user (operator), i.e., aiding execution of a plurality of data acquisition items and image measurement items, which construct an examination operation specified on the basis of an examination request. In this embodiment, the two functions are realized by the first and second examination aid modes.

Figure 45:
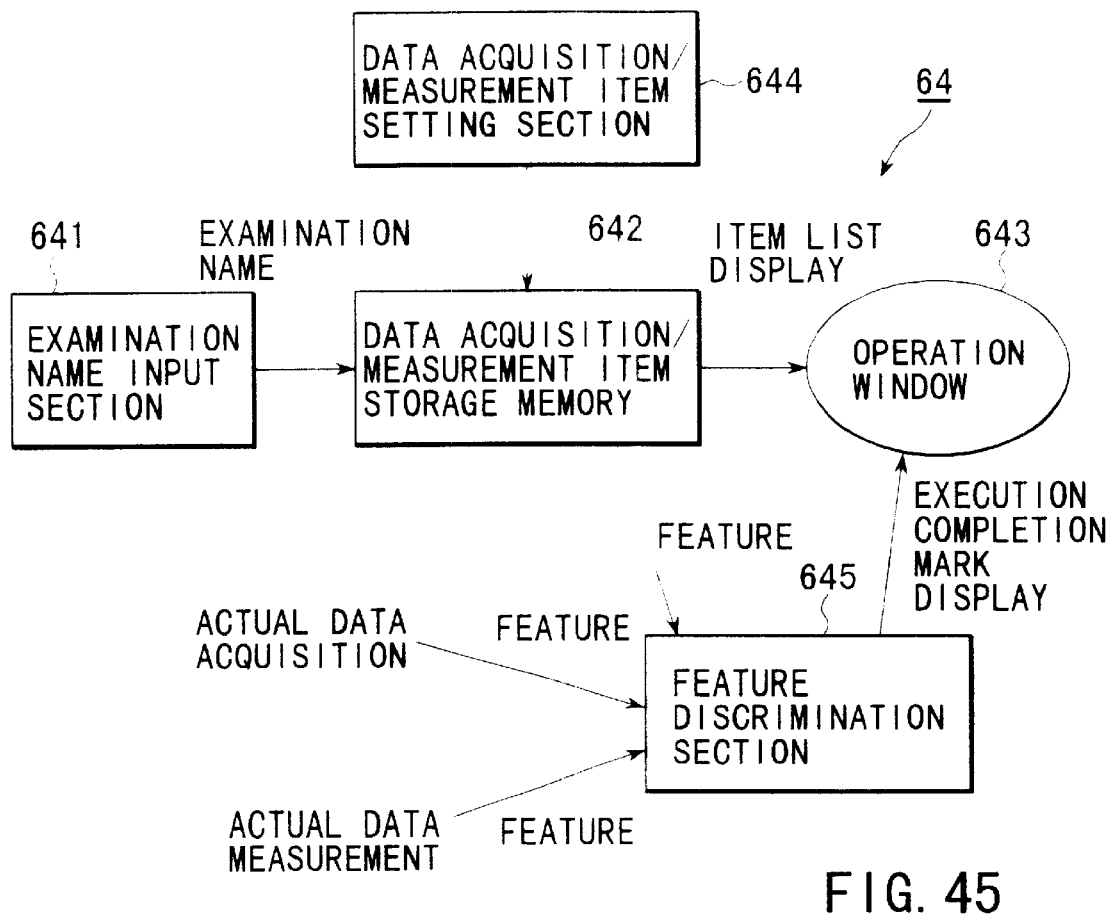
FIG. 45 is a block diagram showing the arrangement of an examination aid function section 64 shown in FIG. 44.

FIG. 45 is a block diagram showing the arrangement of the examination aid function section 64 shown in FIG. 44. As shown in FIG. 45, the examination aid function section 64 comprises an examination name input section 641, data acquisition/measurement item storage memory 642, operation window 643, data acquisition/measurement item setting section 644, and feature discrimination section 645.

First Examination Aid Mode

When an examination order (request) is issued, the name of requested examination is input to the examination name input section 641. The examination name need not always be a name directly representing the examination and may be examination specifying information represented by a numerical code. In this embodiment, the operator operates the panel subsystem 62 to input the examination name to the examination name input section 641. The present invention is not limited to this, and a predetermined examination name may be input to the examination name input section 641 by online communication from another apparatus such as a computer system.

The data acquisition/measurement item storage memory 642 is a storage device for storing a plurality of examination specifying information, and a plurality of data acquisition items or measurement items necessary for an examination operation specified by the examination specifying information.

When an examination starts, the examination name input from the examination name input section 641 is sent to the data acquisition/measurement item storage memory 642. On the basis of the examination name, corresponding pieces of item information are read out from the data acquisition/measurement item storage memory 642. All the readout pieces of item information are sent to the operation window 643 and displayed as a list on the operation window, as shown in FIG. 46.

Data acquisition or measurement need not always be executed in accordance with the display order of the data acquisition/measurement items. The user (operator) can arbitrarily acquire images or accordingly execute measurement with reference to the displayed items.

Figure 46:
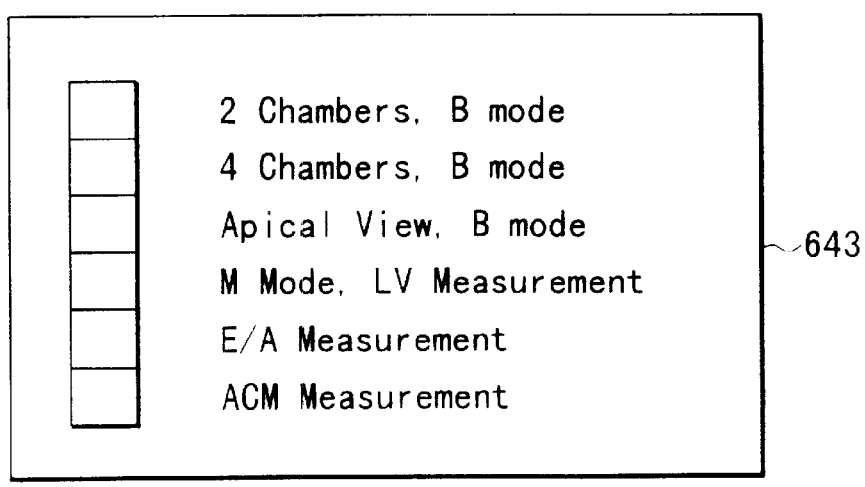
FIG. 46 is a view showing an example of a list of item information.

For the examination specified by the examination name, the displayed list shown in FIG. 46 includes data acquisition/measurement items comprising "2 chambers, B mode", "4 chambers, B mode", "Apical view, B mode", "M mode, LV measurement", "E/A measurement", and "ACM measurement". During the examination, the user can easily know an examination operation that must be executed from this list.

In the above data acquisition/measurement items, the following data acquisition/measurement operations are required. The item "2 chambers, B mode" requests acquisition of B-mode images in which two chambers of a heart are sensed in a similar manner. The item "4 chambers, B mode" requests acquisition of B-mode images in which four chambers of a heart are sensed in a similar manner. The item "Apical view, B mode" requests acquisition of B-mode images of a heart including the apex portion. The "M mode, LV measurement" requests to obtain the inner diameter of the left ventricle from data acquired in the M mode. The "E/A measurement" requests to obtain the ratio of the peak value to the bottom value of data acquired in the PW mode. The "ACM measurement" requests to obtain the cardiac output.

When such a list is used, a skilled operator can easily plan examination operations to be executed in consideration of the most efficient procedure. An inexperienced operator can obtain a sufficient quantity of information necessary for execution of an examination. This is because all items that need be executed can be known at a glance on the list.

This list can be displayed by pressing a list button on the operation panel. For example, when the list button is pressed during displaying an ultrasonic image or measurement window, a list can be displayed for confirmation of the contents.

Data acquisition/measurement items necessary for an examination may be fixed for the apparatus. However, generally, data acquisition/measurement items often change in units of operators or facilities. Preferably, the operator stores item information according to the site (facility) or taste of the operator in the data acquisition/measurement item storage memory 642 using the data acquisition/measurement item setting section 644 before an examination such that the settings can be changed later. With this arrangement, the data acquisition/measurement items can always be set in correspondence with optimum examination contents even when the site or operator changes. Conversely, when pieces of item information are unified in all diagnostic apparatuses in a site, uniform and accurate diagnostic information can be obtained in the facility.

For information of the data acquisition/measurement items stored in the data acquisition/measurement item storage memory 642, attributes representing their features can be designated. For example, in measuring the long and short axial lengths of a left ventricle, the short and long axial lengths construct a feature. When data acquisition or measurement is actually executed (this is determined on the basis of data write in a variable for storage of a measurement result), the feature is sent from the host system 60 to the feature discrimination section 645.

Figure 47:
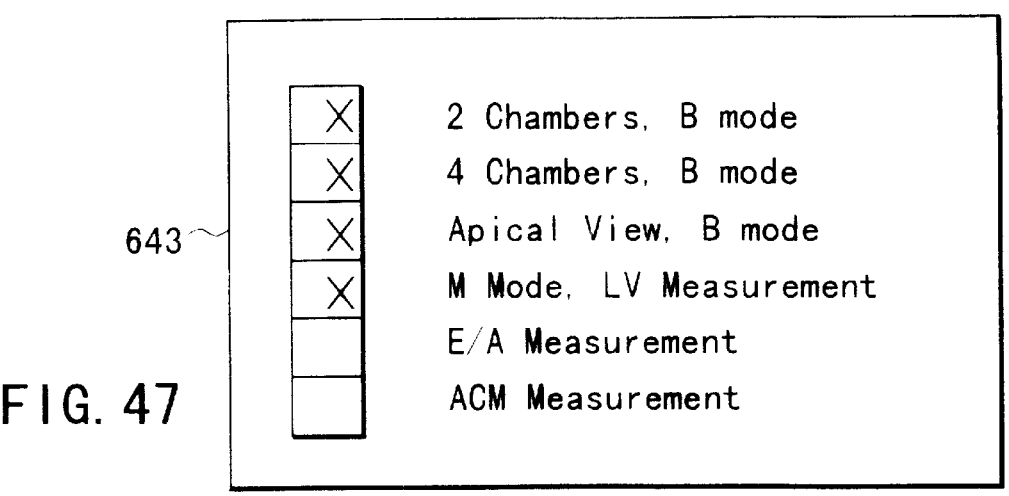
FIG. 47 is a view showing an example of a list with execution completion marks.

The feature discrimination section 645 compares the feature of actually performed data acquisition/measurement with the feature of an item read out from the data acquisition/measurement item storage memory 642, thereby determining the item that has been executed. During execution of an examination, it is determined whether a predetermined item read out from the data acquisition/measurement item storage memory 642 has been executed. The result is sent to the operation window 643, and an execution completion mark is given to a corresponding item (FIG. 47). This feature discrimination is normally automatically performed. However, the execution completion mark may be given on the basis of determination of the operator.

In the example shown in FIG. 47, in items for acquiring images, such as "2 chambers, B mode", "4 chambers, B mode", and "Apical view, B mode", the operator manually gives an execution completion mark, and in items for obtaining values, such as "M mode, LV measurement", "E/A measurement", and "ACM measurement", an execution completion mark is automatically given on the basis of the measurement value. The mode for giving an execution completion mark may be appropriately switched between the automatic mode and the manual mode.

When the operator determines that an examination is ended, all the displayed items must have execution completion marks in principle. When this window is confirmed, omission of a data acquisition/measurement item can be clearly and easily confirmed, unlike the conventional process in which confirmation depends on only the memory of the operator. Hence, a re-examination by calling back a patient can be prevented, and the examination can be efficiently executed.

An operator may intentionally omit an item. In this case, when the operator must do above confirmation at the end of the examination, he/she can easily discriminate intentional omission of an item from omission due to an error. If an unexecuted item remains when completion of the examination is input, a window shown in FIG. 48 should be displayed to caution or warn the operator.

Second Examination Aid Mode

The first examination aid mode intends to execute items in an arbitrary order without forcing the execution order of the items on the operator on the apparatus side. The second examination aid mode is useful as an operation guide system for an especially inexperienced beginner.

In the second examination aid mode, a list of data acquisition/measurement items is not displayed. Instead, item information representing a plurality of data acquisition items or measurement items necessary for an examination operation specified by examination specifying information are sequentially displayed at least one by one.

FIG. 48 is a view showing an example of display in the second examination aid mode. Referring to FIG. 48, for example, item information ("E/A measurement") to be executed next is displayed on the operation window 643.

This second examination aid mode functions as an operation guide system for sequentially displaying an item which is to be executed next (or may be skipped), even an inexperienced operator can easily use the apparatus.

As has been described above, according to the ultrasonic diagnostic apparatus of the present invention, data acquisition and measurement items are executed without omission, and an accurate examination is properly performed. More specifically, an increase in human errors that the operator often forgets to execute a necessary item can be suppressed. In addition, a deterioration in examination accuracy due to omission of an item can be prevented, and a re-examination of a patient later can be prevented.

The present invention is not limited to the above-described embodiments, and various changes and modifications can be made, as will be described below.

(1) Information associated with a list of measurement items can be transmitted/received between sites through a network. This function is effective, for example, when uniform and accurate diagnosis is required in different sites. This is because the diagnostic items can be unified by transmitting/receiving list information through a network.

(2) Each aid mode can also be applied to, e.g., a diagnostic operation according to a workflow already described in the first embodiment. For example, assume that the first examination aid mode is applied in executing the activity "Measure". In this case, a new activity is defined in which "an operation associated with measurement is manually performed by the user, and the list of measurement items is displayed to check only omission of a measurement item". A workflow containing this activity only need be prepared.

Additional advantages and modifications will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents.

What is claimed is:

1. An ultrasonic diagnostic apparatus comprising:
   a storage section configured to store a plurality of operation procedures which are defined by arrangement of activities related to at least one of functions of said ultrasonic diagnostic apparatus in a predetermined order;
   a selection section configured to select an operation procedure in said storage section on the basis of input information;
   a display section configured to display the operation procedure selected by said selection section; and
   a controller configured to execute each operation corresponding to each activity in accordance with the displayed operation procedure.

2. The apparatus according to claim 1, wherein said display section displays the selected operation procedure and an ultrasonic image simultaneously.

3. The apparatus according to claim 1, wherein said display section controls a display form of an activity which composes the displayed operation procedure in accordance with an execution state of the displayed operation procedure.

4. The apparatus according to claim 1, wherein said display section controls a display form of each of activities which composes the displayed operation procedure depending on whether a state of each of the activities is "unexecuted", "execution in progress", "normal end", "abnormal end", "interrupt", or "re-execute".

5. The apparatus according to claim 1, wherein said display section displays aid information associated with an activity which composes the displayed operation procedure.

6. The apparatus according to claim 5, wherein said display section displays, as the aid information, at least one of an anatomical view, a representative example of an ultrasonic image, a manual of said ultrasonic diagnostic apparatus, a description of contents of the operation, and a description of a clinical application.

7. The apparatus according to claim 5, wherein said storage section stores information with respect to a correspondence between the aid information displayed on said display section and a predetermined activity; and
   said controller executes a control of the predetermined activity corresponding to the aid information on the basis of the information of correspondence.

8. The apparatus according to claim 1, further comprising a parameter setting section (r) which sets a parameter associated with an activity composing the displayed operation procedure, the parameter performing a predetermined operation for a predetermined activity of the operation procedure displayed on said display section.

9. The apparatus according to claim 1, wherein said controller can control said ultrasonic diagnostic apparatus on the basis of a plurality of activities.

10. The apparatus according to claim 1, further comprising a comparing section configured to compare the displayed operation procedure with a predetermined operation procedure stored in said storage section, and wherein said display section further has a function of displaying a comparison result between the displayed operation procedure and the predetermined operation procedure.

11. The apparatus according to claim 1, further comprising a comparing section configured to compare a result associated with diagnosis according to the displayed operation procedure with diagnostic information stored in advance, and wherein said display section has a function of displaying a comparison result between the result associated with diagnosis according to the displayed operation procedure and the diagnostic information stored in advance.

12. The apparatus according to claim 1, further comprising a manual operation section configured to change the predetermined order of the arrangement of activities in displayed operation procedure, and wherein said controller executes each operation corresponding to each activity in accordance with the changed and displayed operation procedure.

13. The apparatus according to claim 1, wherein at least one of the activities is an activity with respect to scan mode, an activity with respect to measurement, an activity with respect to storage of data or an activity with respect to printing out of data.

14. The apparatus according to claim 1, wherein the activities include a plurality of activities, each of which changes scan condition.

15. An ultrasonic diagnostic apparatus comprising:

a storage section configured to store a plurality of operation procedures which are defined by arrangement of activities related to at least one of functions of said ultrasonic diagnostic apparatus in a predetermined order;

a selection section configured to select an operation procedure in said storage section on the basis of input information;

a display section configured to display the operation procedure selected by said selection section;

an activity selection section for selecting an activity which composes the displayed operation procedure, in accordance with an instruction by an operator; and a controller configured to execute an operation corresponding to the activity according to the displayed operation procedure in order and, if an activity is selected by said activity selection section, executing an operation corresponding to the activity selected by said activity selection section.

16. An ultrasonic diagnostic apparatus comprising:

a storage section configured to store a plurality of operation procedures which are defined by arrangement of activities related to at least one of functions of said ultrasonic diagnostic apparatus in a predetermined order;

an input section configured to input information for selecting the operation procedure;

a display section configured to display the operation procedure selected by said input section;

a change section configured to change composition of the displayed operation procedure in a case that a predetermined activity is added to the displayed operation procedure or is omitted from the displayed operation procedure under the execution of the displayed operation procedure; and a controller configured to execute an operation corresponding to the activity which composes a changed operation procedure in the case that the displayed operation procedure is changed by said change section.

17. An ultrasonic diagnostic apparatus comprising:

a storage section configured to store a plurality of operation procedures which are defined by arrangement of activities related to at least one of functions of said ultrasonic diagnostic apparatus in a predetermined order;

a selection section configured to select an operation information in said storage section on the basis of input information;

a selection section configured to select an operation procedure from the plurality of operation procedures on the basis of the information;

a display section configured to display the operation procedure selected by said selection section and, if an activity selected by an operator is associated with a sub-operation procedure, displaying the sub-operation procedure; and a controller configured to execute control of an activity selected from the activities which compose the displayed operation procedure or the displayed sub-operation procedure.

18. The apparatus according to claim 17, wherein said display section displays simultaneously or selectively the operation procedure and the sub-operation procedure.

19. The apparatus according to claim 18, wherein the operation procedure includes branches of an operation to execute each activity which composes the branched operations.

20. The apparatus according to claim 18, wherein said display section controls a display form of each branch of operation included by the displayed operation procedure in accordance with frequency.

21. The apparatus according to claim 18, wherein the displayed operation procedure includes branches of an operation, from which a next operation is selected in accordance with a predetermined condition table.

22. The apparatus according to clam 18, wherein the operation procedure includes branches of an operation, from which a next operation is selected by inquiring of a predetermined database.

23. The apparatus according to claim 17, wherein said display section discriminates a display form between the operation procedure and the sub-operation procedure.

24. The apparatus according to claim 17, wherein said display section displays hierarchically an associated sub-operation procedure if an activity which composes the displayed sub-operation procedure is associated with a sub-operation procedure.

25. An ultrasonic diagnostic apparatus comprising:

a storage section for storing a plurality of operation procedures, at least one of which contains branched operations and is defined by arrangement of activities related to at least one of functions of said ultrasonic diagnostic apparatus in a predetermined order;

an input section for inputting predetermined information relating to diagnosis;

a selection section for selecting an operation procedure from the plurality of operation procedures on the basis of the information;

a display section for displaying the operation procedure selected by said selection section in such a manner that the selected operation procedure contains branches of an operation; and a controller configured to execute an operation corresponding to each activity in order according to the displayed operation procedure.

26. The apparatus according to claim 25, wherein the operation procedure includes branches of an operation to select by manual operation.

27. An ultrasonic diagnostic apparatus comprising:
a storage section configured to store a plurality of examination item lists corresponding to a plurality of data acquisition items and measurement items;
a selection section configured to select an examination item list from the plurality of examination item lists,
a data acquisition and measurement section configured to execute data acquisition and a measurement corresponding to a data acquisition item and a measurement item on the selected examination item list; and
a display section configured to display simultaneously the data acquisition item and the measurement item corresponding to the selected examination item list and a mark which represents whether the data acquisition or the measurement is executed; and
a change section configured to change whether the displayed acquisition or the displayed measurement is executed, by manual operation.

28. The apparatus according to claim 27, further comprising item change section configured to change at least one of the number of display items, a display order, and a type of display item in respect of the data acquisition items or the measurement items displayed simultaneously on said display section.

29. The apparatus according to claim 27, wherein said display section displays sequentially the data acquisition items and the measurement items corresponding to the selected examination item list at least one by one.

30. The apparatus according to claim 27, further comprising a determination section configured to determine completion of execution of each displayed data acquisition item or measurement item on the basis of a feature associated with data acquisition or measurement; and
whereby said display section displays each displayed data acquisition item or measurement item with giving a mark on the basis of the result determined by said determination section.

31. The apparatus according to claim 30, wherein said display section displays a list of item information added with the marks for confirmation immediately before an end of the examination.

32. An ultrasonic diagnostic apparatus comprising:
a storage section configured to store a plurality of examination lists corresponding to a plurality of data acquisition items and measurement items;
a selection section configured to select an examination item list from the plurality of examination item lists,
a data acquisition and measurement section configured to execute data acquisition and a measurement corresponding to the data acquisition item and the measurement item on the selected examination item list; and
a display section configured to display simultaneously the data acquisition item and the measurement item corresponding to the selected examination item list and a mark which represents whether each of the data acquisitions and the measurements is executed; and
a communication section configured to transmit/receive information of the examination item list through a network.

33. An ultrasonic diagnostic apparatus comprising:
a storage section configured to store a plurality of operation procedures formed of activities which is defined by arrangement of a plurality of data acquisition items and measurement items in a predetermined order,
a controller configured to execute data acquisitions and measurements corresponding to the plurality of the data acquisition items and the measurement items on the plurality of the examination item lists; and
an output section configured to output data in respect of the plurality of the data acquisition items and the measurement items in a predetermined format.

34. The apparatus according to claim 33, further comprising a display section configured to display an ultrasound image associated with data acquisition or measurement.

35. The apparatus according to claim 33, further comprising a communication section configured to transmit/receive information of the examination item list through a network.

36. The apparatus according to claim 33, further comprising a storage section configured to store a plurality of data of the data acquisition items and the measurement items associated with each other.

37. A control method of a ultrasonic diagnostic apparatus comprising:
selecting a predetermined operation procedure from a plurality of operation procedures stored in advance, which are defined by arrangement of activities related to at least one of functions of said ultrasonic diagnostic apparatus in a predetermined order on the basis of information relating to diagnosis;
displaying the selected operation procedure; and
executing each operation corresponding to each activity in accordance with the displayed operation procedure.

38. A control method of an ultrasonic diagnostic apparatus comprising:
selecting a predetermined operation procedure from a plurality of operation procedures stored in advance, which are defined by arrangement of activities related to at least one of functions of said ultrasonic diagnostic apparatus in a predetermined order on the basis of information relating to diagnosis;
displaying the selected operation procedure;
selecting an activity which composes the displayed operation procedure, in accordance with an instruction by an operator;
executing each operation corresponding to each activity in accordance with the displayed operation procedure in order; and
executing an operation corresponding to a selected activity if another activity is selected in progress of each operation.

39. A control method of an ultrasonic diagnostic apparatus comprising:
selecting a predetermined operation procedure from a plurality of operation procedures stored in advance, which are defined by arrangement of activities related to at least one of functions of said ultrasonic diagnostic apparatus in a predetermined order on the basis of information relating to diagnosis;
displaying the selected operation procedure;
selecting an activity which composes the displayed operation procedure, in accordance with an instruction by an operator;
changing composition of the displayed operation procedure in such a manner that a predetermined activity is added to the displayed operation procedure or is omitted from the displayed operation procedure under the execution of the displayed operation procedure; and executing an operation corresponding to the activity which composes a changed operation procedure.

40. A control method of an ultrasonic diagnostic apparatus comprising:

selecting a predetermined operation procedure from a plurality of operation procedures stored in advance, each of which is defined by arrangement of activities related to at least one of functions of said ultrasonic diagnostic apparatus in a predetermined order on the basis of information relating to diagnosis;

displaying the selected operation procedure;

displaying a sub-operation procedure if an activity selected by an operator, which composes the displayed operation procedure, is associated with a sub-operation procedure; and executing control of the activity selected from the activities which compose the displayed operation procedure or the displayed sub-operation procedure.

41. A control method of an ultrasonic diagnostic apparatus comprising:

selecting a predetermined operation procedure from a plurality of operation procedures stored by storage section, each of which contains branched operations and is defined by arrangement of activities related to at least one of functions of said ultrasonic diagnostic apparatus in a predetermined order, on the basis of inputted information relating to diagnosis;

displaying the selected operation procedure in such a manner that the selected operation procedure contains branches of an operation; and executing an operation corresponding to the each of activities in order according to the displayed operation procedure.

42. A control method of an ultrasonic diagnostic apparatus comprising:

selecting a predetermined examination item list from a plurality of examination item lists, stored in advance, which corresponds to a plurality of data acquisition items and measurement items;

executing each data acquisition and a measurement in respect to each of the data acquisition item and the measurement item composes the selected examination item list;

displaying simultaneously the data acquisition item and the measurement item corresponding to the selected examination item list and a mark which represents whether the data acquisition or the measurement is executed; and changing the mark which represents whether the displayed acquisition or the displayed measurement is executed by manual operation.

43. A control method of an ultrasonic diagnostic apparatus comprising:

selecting an examination item list from a plurality of examination lists which is stored in advance and is composed of a plurality of data acquisition items and measurement items;

executing data acquisition and a measurement corresponding to the data acquisition item and the measurement item on the selected examination item list; and displaying simultaneously the data acquisition item and the measurement item corresponding to the selected examination item list and a mark which represents whether each of the data acquisitions and the measurements is executed; and transmitting/receiving information of the examination item list through a network.

44. A control method of an ultrasonic diagnostic apparatus comprising:

executing data acquisitions and measurements corresponding to a plurality of operation procedures which are stored in advance and defined by arrangement of a plurality of data acquisition items and measurement items in a predetermined order; and outputting data in respect of the plurality of the data acquisition items and the measurement items in a predetermined format.

* * * * *